United States Patent
Nerkamp et al.

(10) Patent No.: US 9,492,572 B2
(45) Date of Patent: *Nov. 15, 2016

(54) DIMERIC BINDING PROTEINS BASED ON MODIFIED UBIQUITINS

(75) Inventors: Joerg Nerkamp, Halle/Saale (DE); Eva Bosse-Doenecke, Halle/Saale (DE); Arnd Steuernagel, Halle/Saale (DE); Ulrike Fiedler, Halle/Saale (DE); Markus Fiedler, Halle/Saale (DE)

(73) Assignee: Scil Proteins GmbH, Halle/Saale ( * ) Notice: Subject to any disclaimer, the term of this patent is extended or adjusted under 35 U.S.C. 154(b) by 207 days.

This patent is subject to a terminal disclaimer.

(21) Appl. No.: 14/126,358

(22) PCT Filed: Jun. 15, 2012

(86) PCT No.: PCT/EP2012/061455
§ 371 (c)(1),
(2), (4) Date: Dec. 13, 2013

(87) PCT Pub. No.: WO2012/172055
PCT Pub. Date: Dec. 20, 2012

(65) Prior Publication Data
US 2014/0127129 A1    May 8, 2014

(30) Foreign Application Priority Data
Jun. 15, 2011  (EP) .................................... 11170054

(51) Int. Cl.
  C07K 19/00       (2006.01)
  A61K 51/08       (2006.01)
  C12N 1/14        (2006.01)
  (Continued)

(52) U.S. Cl.
CPC ............... *A61K 51/08* (2013.01); *C07K 14/00*
(2013.01); *C07K 14/47* (2013.01); *C12N 1/14*
(2013.01); *C12N 1/16* (2013.01); *C12N 1/20*
(2013.01); *C12N 15/62* (2013.01); *C12N 15/63* (2013.01); *G01N 33/6803* (2013.01);
(Continued)

(58) Field of Classification Search
None
See application file for complete search history.

(56) References Cited

U.S. PATENT DOCUMENTS 4,873,192 A  10/1989  Kunkel
5,789,166 A   8/1998  Bauer et al.
(Continued)

FOREIGN PATENT DOCUMENTS

RU        2134696 C1    8/1999
WO      WO2005/044845   5/2005
(Continued)

OTHER PUBLICATIONS

Abedi et al., "Green fluorescent protein as a scaffold for intracellular presentation of peptides," Nucleic Acids Research. vol. 26, No. 2 pp. 623-630 (1998).
(Continued)

*Primary Examiner* — Robert Mondesi
*Assistant Examiner* — Richard Ekstrom
(74) *Attorney, Agent, or Firm* — Jenkins, Wilson, Taylor & Hunt, P.A.

(57) ABSTRACT

The present invention refers to novel dimeric proteins obtained from modified ubiquitin capable of binding targets with high affinity. The novel dimeric binding proteins comprise a combination of amino acid substitutions and at least one insertion of amino acids in one of the monomers. The invention is further directed to the use of said proteins in medical diagnosis or treatment methods.

21 Claims, 4 Drawing Sheets

(51) Int. Cl.

| | | |
|---|---|---|
| C12N 15/62 | (2006.01) | |
| C12N 15/63 | (2006.01) | |
| C12N 1/16 | (2006.01) | |
| C12N 1/20 | (2006.01) | |
| C07K 14/47 | (2006.01) | |
| C07K 14/00 | (2006.01) | |
| G01N 33/68 | (2006.01) | |

(52) U.S. Cl.
CPC ...... C07K 2319/00 (2013.01); C07K 2319/33 (2013.01); C07K 2319/95 (2013.01)

(56) References Cited

U.S. PATENT DOCUMENTS

| | | | |
|---|---|---|---|
| 5,958,684 | A | 9/1999 | Van Leeuwen et al. |
| 6,217,863 | B1 | 4/2001 | Godavarti et al. |
| 6,569,677 | B1 | 5/2003 | Legrand et al. |
| 6,620,587 | B1 | 9/2003 | Taussig et al. |
| 6,673,901 | B2 | 1/2004 | Koide |
| 6,799,121 | B2 | 9/2004 | Chu et al. |
| 7,250,297 | B1 | 7/2007 | Beste et al. |
| 7,273,924 | B1 | 9/2007 | Neri et al. |
| 7,393,918 | B2 | 7/2008 | Golemi-Kota et al. |
| 7,601,803 | B1 | 10/2009 | Fiedler et al. |
| 7,838,629 | B2 | 11/2010 | Fiedler et al. |
| 7,851,599 | B2 | 12/2010 | Menrad et al. |
| 8,097,254 | B2 | 1/2012 | Neri et al. |
| 8,404,814 | B2 | 3/2013 | Neri et al. |
| 8,426,357 | B2 | 4/2013 | Kraehmer et al. |
| 8,455,625 | B2 | 6/2013 | Neri et al. |
| 8,592,179 | B2 | 11/2013 | Schraeml et al. |
| 8,623,373 | B2 | 1/2014 | Zardi et al. |
| 8,748,351 | B2* | 6/2014 | Kunert ............. C07K 14/525 435/320.1 |
| 8,790,895 | B2 | 7/2014 | Fiedler et al. |
| 8,921,304 | B2* | 12/2014 | Steuernagel ......... C07K 14/525 514/1.1 |
| 2003/0045681 | A1 | 3/2003 | Neri et al. |
| 2003/0073623 | A1 | 4/2003 | Drmanac et al. |
| 2004/0043386 | A1 | 3/2004 | Pray et al. |
| 2006/0058510 | A1 | 3/2006 | Skerra et al. |
| 2007/0015248 | A1 | 1/2007 | Anton et al. |
| 2007/0189963 | A1 | 8/2007 | Neri et al. |
| 2008/0171851 | A1* | 7/2008 | Fiedler ............. C07K 14/00 530/324 |
| 2010/0119446 | A1 | 5/2010 | Grabulovski et al. |
| 2012/0244596 | A1 | 9/2012 | Skerra et al. |
| 2012/0301393 | A1 | 11/2012 | Steuernagel et al. |
| 2013/0097737 | A1 | 4/2013 | Kovalic et al. |
| 2014/0219959 | A1 | 8/2014 | Nerkamp et al. |
| 2015/0183846 | A1 | 7/2015 | Lange et al. |

FOREIGN PATENT DOCUMENTS

| | | |
|---|---|---|
| WO | WO2007/054120 | 5/2007 |
| WO | WO2012/171541 | 12/2012 |
| WO | WO2013/186329 | 12/2013 |

OTHER PUBLICATIONS

Advisory Action corresponding to U.S. Appl. No. 10/030,605 dated Oct. 13, 2006.
Advisory Action corresponding to U.S. Appl. No. 11/732,632 dated Jun. 30, 2010.
Advisory Action corresponding to U.S. Appl. No. 12/072,959 dated May 18, 2010.
Baker et al., "Protein Expression Using Cotranslational Fusion and Cleavage of Ubiquitin," The Journal of Biological Chemistry. vol. 269, No. 41 pp. 25381-25386 (1994).
Beal et al., "Surface hydrophobic residues of multiubiquitin chains essential for proteolytic targeting," PNAS. vol. 93 pp. 861-866 (1996).
Beste et al., "Small antibody-like proteins with prescribed ligand specificities derived from the lipocalin fold," PNAS. vol. 96 pp. 1898-1903 (1999).
Birchler et al., "Selective targeting and photocoagulation of ocular aniogenesis mediated by a phage-derived human antibody fragment," Nature Biotechnology. vol. 17 pp. 984-988 (1999).
Bird et al., "Single-Chain Antigen-Binding Proteins," Science. vol. 242 pp. 423-426 (1988).
Bofill et al., "Engineering Stabilising beta-Sheet Interactions into a Conformationally Flexible Region of the Folding Transition State of Ubiquitin," Journal of Molecular Biology. vol. 353, No. 2 pp. 373-384 (2005).
Bolton et al., "Structure and Properties of a Dimeric N-terminal Fragment of Human Ubiquitin," Journal of Molecular Biology. vol. 314, No. 4 pp. 773-787 (2001).
Borsi et al., "Selective targeted delivery of TNFα to tumor blood vessels," Blood. vol. 102, No. 13 pp. 4384-4392 (2003).
Brinkmann et al., "A recombinant immunotoxin containing a disulfide-stabilized Fv-fragment," PNAS. vol. 90 pp. 7538-7542 (1993).
Brinkmann et al., "Stabilization of a Recombinant Fv Fragment by Base-Loop Interconnection and VH-VL Permutation," Journal of Molecular Biology. vol. 268 pp. 107-117 (1997).
Buchberger et al., "The UBX Domain: A Widespread Ubiquitin-Like Module," Journal of Molecular Biology. vol. 307, No. 1 pp. 17-24 (2001).
Burch, T.J., and Haas, A.L., "Site-directed mutagenesis of ubiquitin. Differential roles for arginine in the interaction with ubiquitin-activating enzyme," Biochemistry. vol. 33, No. 23 pp. 7300-7308 (1994) [ABSTRACT].
Campion et al., "Biochemical Properties of Site-Directed Mutants of Human Epidermal Growth Factor: Importance of Solvent-Exposed Hydrophobic Residues of the Amino-Terminal Domain in Receptor Binding," Biochemistry. vol. 29, No. 42 pp. 9988-9993 (1990).
Connolly, "Solvent-Accessible Surfaces of Proteins and Nucleic Acids." Science. vol. 221, No. 4612 pp. 709-713 (1983).
Corrected Notice of Allowability corresponding to U.S. Appl. No. 11/656,646 dated Sep. 26, 2013.
Daugherty et al., "Antibody affinity maturation using bacterial surface display," Protein Engineering. vol. 11, No. 9 pp. 825-832 (1998).
de Kruif et al., "Selection and Application of Human Single Chain Fv Antibody Fragments from a Semi-synthetic Phage Antibody Display Library with Designed CDR3 Regions," Journal of Molecular Biology. vol. 248 pp. 97-105 (1995).
Decision to Grant corresponding to Rusian Patent Application No. 2012115491/10(023353) dated Nov. 20, 2014.
Deed of Grant corresponding to Autralian Patent No. 2010332932 dated May 2, 2013.
Deed of Grant corresponding to Australian Patent No. 2010332938 dated Apr. 4, 2013.
Dikic et al., "Ubiquitin-binding domains—from structures to functions," Nature Reviews. vol. 10 pp. 659-671 (2009).
Dubin et al., "Balloon Catheterization Induces Arterial Expression of Embryonic Fibronectins," Arterosclerosis, Thrombosis, and Vascular Biology. vol. 15 pp. 1958-1967 (1995).
Ebersbach et al., "Affilin-Novel Binding Molecules Based on Human (—B-Crystallin, an All (—Sheet Protein," Journal of Molecular Biology. vol. 372 pp. 172-185 (2007).
Ecker et al., "Gene Synthesis, Expression, Structures, and Functional Activities of Site-specific Mutants of Ubiquitin," The Journal of Biological Chemistry. vol. 262, No. 29 pp. 14213-14221 (1987).
Ermolenko et al., "Noncharged amino acid residues at the solvent-exposed positions in the middle and at the C terminus of the alpha-helix have the same helical propensity," Protein Science. vol. 12, No. 6 pp. 1169-1176 (2003).
European Search Report corresponding to European Patent Application No. 06 118 519.5-2401 dated Apr. 2, 2007.
European Search Report corresponding to European Patent Application No. 09 176 574.3-2401 dated Jan. 18, 2010.
European Search Report corresponding to European Patent Application No. 10 181 802.9-2401 dated Feb. 10, 2011.

(56) References Cited

OTHER PUBLICATIONS

Fiedler et al., "Affilintm Molecules: Novel Ligands for Bioseparation," Food and Bioproducts Processing. vol. 84, No. C1 pp. 3-8 (2006).
Finucane et al., "Core-Directed Protein Design. I. An Experimental Method for Selecting Stable Proteins from Combinatorial Libraries," Biochemistry. vol. 38 pp. 11604-11612 (1999).
Finucane et al., "Core-Directed Protein Design. II. Rescue of a Multiply Mutated and Destabilized Variant of Ubiquitin." Biochemistry. vol. 38, No. 36 pp. 11613-11623 (1999).
Gebauer, M., and Skerra, A., "Engineered protein scaffolds as next-generation antibody therapeutics," Current Opinion in Chemical Biology. vol. 13, No. 3 pp. 245-255 (2009).
Grabulovski et al., "A Novel, Non-immunogenic Fyn SH3-derived Binding Protein with Tumor Vascular Targeting Properties," The Journal of Biological Chemistry. vol. 282, No. 5 pp. 3196-3204 (2007).
Guo et al., "Protein tolerance to random amino acid change," PNAS. vol. 101, No. 25 pp. 9205-9210 (2004).
Hanes et al., "Picomolar affinity antibodies from a fully synthetic naive library selected and evolved by ribosome display," Nature Biotechnology. vol. 18 pp. 1287-1292 (2000).
Hanes et al., "Ribosome display efficiently selects and evolves high-affinity antibodies in vitro from immune libraries," PNAS. vol. 95 pp. 14130-14135 (1998).
Hanes, J., and Plückthun, A., "In vitro selection and evolution of functional proteins by using ribosome display," PNAS. vol. 94, No. 10 pp. 4937-4942 (1997).
He, M., and Taussig, M.J., "Antibody-ribosome-mRNA (ARM) complexes as efficient selection particles for in vitro display and evoluation of antibody combining sites," Nucleic Acids Research. vol. 25, No. 24 pp. 5132-5134 (1997).
Hershko, A., and Ciechanover, A., "The Ubiquitin System," Annu. Rev. Biochem. vol. 67 pp. 425-479 (1998).
Hey et al., "Artificial, non-antibody binding proteins for pharmaceutical and industrial applications," TRENDS in Biotechnology. vol. 23, No. 10 pp. 514-522 (2005).
http://scop.mrc-lmb.cam.ac.uk/scop/data/scop.b.e.ca.html, "Fold: beta-Grasp (ubiquitin-like)," Mar. 15, 2004. [ABSTRACT].
Intent to Grant correponding to European Patent Application No. EP 10 787 815.9-1410 dated Aug. 13, 2013.
International Preliminary Report on Patentability (Chapter I of the Patent Cooperation Treaty) corresponding to International Patent Application No. PCT/EP2007/062375 dated May 19, 2009.
International Preliminary Report on Patentability (Chapter I of the Patent Cooperation Treaty) corresponding to International Patent Application No. PCT/EP2010/069665 dated Jun. 19, 2012.
International Preliminary Report on Patentability corresponding to International Patent Application No. PCT/EP2004/005730 dated May 13, 2005.
International Search Report corresponding to International Patent Application No. PCT/EP2000/006698 dated Feb. 2, 2001.
International Search Report corresponding to International Patent Application No. PCT/EP2004/005730 dated Oct. 5, 2004.
International Search Report corresponding to International Patent Application No. PCT/EP2005/010932 dated Apr. 11, 2006.
International Search Report corresponding to International Patent Application No. PCT/EP2007/062375 dated Apr. 25, 2008.
International Search Report corresponding to International Patent Application No. PCT/EP2010/069665 dated Apr. 13, 2011.
International Search Report corresponding to International Patent Application No. PCT/EP2010/069674 dated Jun. 17, 2011.
International Search Report corresponding to International Patent Application No. PCT/EP2011/002962 dated Mar. 19, 2012.
International Search Report corresponding to International Patent Application No. PCT/EP2012/061455 dated Oct. 25, 2012.
International Search Report corresponding to International Patent Application No. PCT/EP2012/061459 dated Sep. 24, 2012.
International Search Report corresponding to International Patent Application No. PCT/EP2013/062310 dated Aug. 2, 2013.
Jackson, "Ubiquitin: a small protein folding paradigm." Org. Biomol. Chem. vol. 4, No. 10 pp. 1845-1853 (2006).
Kaczmarek et al., "Distribution of Oncofetal Fibronectin Isoforms in Normal, Hyperplastic and Neoplastic Human Breast Tissues," International Journal of Cancer. vol. 58 pp. 11-16 (1994).
Khorasanizadeh et al., "Folding and stability of a tryptophan-containing mutant of ubiquitin." Biochemistry. vol. 32, No. 27 pp. 7054-7063 (1993).
Kieke et al., "Isolation of anti-T cell receptor scFv mutants by yeast surface display," Protein Engineering. vol. 10, No. 11 pp. 1303-1310 (1997).
Kiel, C., and Serrano, L., "The Ubiquitin Domain Superfold: Structure-based Sequence Alignments and Characterization of Binding Epitopes," Journal of Molecular Biology. vol. 355, No. 4 pp. 821-844 (2006).
Knappik et al., "Fully Synthetic Human Combinatorial Antibody Libraries (HuCAL) Based on Modular Consensus Frameworks and CDRs Randomized with Trinucleotides," Journal of Molecular Biology. vol. 296 pp. 57-86 (2000).
Koide et al., "The Fibronectin Type III Domain as a Scaffold for Novel Binding Proteins," Journal of Molecular Biology. vol. 284 pp. 1141-1151 (1998).
Krantz et al., "Discerning the Structure and Energy of Multiple Transition States in Protein Folding using ψ—Analysis," Journal of Molecular Biology. vol. 337, No. 2 pp. 463-475 (2004).
Krippner-Heidenreich et al., "Single-chain TNF, a TNF derivative with enhanced stability and antitumoral activity," Journal of Immunology, vol. 180, pp. 8176-8183 (2008).
Ku, J., and Schultz, P.G., "Alternate protein frameworks for molecular recognition," PNAS. vol. 92 pp. 6552-6556 (1995).
Larsen et al., "The Ubiquitin Superfamily: Members, Features, and Phylogenies," Journal of Proteome Research. vol. 1 pp. 411-419 (2002).
Laub et al., "Localized solution structure refinement of an F45W variant of ubiquitin using stochastic boundary molecular dynamics and NMR distance restraints," Protein Science. vol. 4 pp. 973-982 (1995).
Lazar, C.N., and Wang, H., "De novo design of the hydrophobic core of ubiquitin," Protein Science. vol. 6 pp. 1167-1178 (1997).
Lipovsek, D., and Plückthun, A., "In-vitro protein evolution by ribosome display and mRNA display," Journal of Immunological Methods. vol. 290 pp. 51-67 (2004).
Lo et al., "Structural Basis for Recognition of Diubiquitins by NEMO," Molecular Cell. vol. 33 pp. 602-615 (2009).
Loladze et al., "Both helical propensity and side-chain hydrophobicity at a partially exposed site in alpha-helix contribute to the thermodynamic stability of ubiquitin," Proteins. vol. 58, No. 1 pp. 1-6 (2005).
Mayr et al., "Domain Interactions and Connecting Peptides in Lens Crystallins," Journal of Molecular Biology. vol. 235 pp. 84-88 (1994).
McConnell, S.J., and Hoess, R.H. "Tendamistat as a Scaffold for Conformationally Constrained Phage Peptide Libraries," The Journal of Molecular Biology. vol. 250 pp. 460-470 (1995).
Miura et al., "Characterization of the Binding Interface between Ubiquitin and Class I Human Ubiquitin-conjugating Enzyme 2b by Multidimensional Heteronuclear NMR Spectroscopy in Solution," Journal of Molecular Biology. vol. 290 pp. 213-228 (1999).
Müller et al., "SUMO, ubiquitin's mysterious cousin," Nat. Rev. Mol. Cell Biol. vol. 2 pp. 202-210 (2001).
Müller, H.N., and Skerra, A., "Grafting of a High-Affinity Zn(II)-Binding Site on the β-Barrel of Retional-Binding Protein Results in Enhanced Folding Stability and Enables Simplified Purification," Biochemistry. vol. 33, No. 47 pp. 14126-14135 (1994).
Notice of Allowance corresponding to U.S. Appl. No. 10/030,605 dated Apr. 14, 2009.
Notice of Allowance corresponding to U.S. Appl. No. 11/283,332 dated Jun. 6, 2014.
Notice of Allowance corresponding to U.S. Appl. No. 11/656,646 dated Aug. 27, 2013.
Notice of Allowance corresponding to U.S. Appl. No. 11/732,632 dated Aug. 23, 2010.

(56) References Cited

OTHER PUBLICATIONS

Notice of Allowance corresponding to U.S. Appl. No. 12/072,959 dated Jun. 3, 2014.
Notice of Allowance corresponding to U.S. Appl. No. 12/514,550 dated Sep. 10, 2013.
Notice of Allowance corresponding to U.S. Appl. No. 13/142,195 dated Aug. 4, 2014.
Notice of Allowance corresponding to U.S. Appl. No. 13/144,809 dated Mar. 3, 2014.
Notification Concerning Transmittal of International Preliminary Report on Patentability (Chapter I of the Patent Cooperation Treaty) corresponding to International Patent Application No. PCT/EP2010/069666 dated Jun. 28, 2012.
Notification Concerning Transmittal of International Preliminary Report on Patentability (Chapter I of the Patent Cooperation Treaty) corresponding to International Patent Application No. PCT/EP2010/069674 dated Jun. 28, 2012.
Notification of Transmittal of Translation of the International Preliminary Report on Patentability (Chapter I of the Patent Cooperation Treaty) corresponding to International Patent Application No. PCT/EP2004/005730 dated Apr. 13, 2006.
Notification of Transmittal of Translation of the International Preliminary Report on Patentability (Chapter I or Chapter II of the Patent Cooperation Treaty) corresponding to International Patent Application No. PCT/EP2005/010932 dated May 3, 2007.
Nygren, P., and Uhlen, M., "Scaffolds for engineering novel binding sites in proteins," Current Opinion in Structural Biology. vol. 7 pp. 463-469 (1997).
Office Action corresponding to Australian Patent Application No. 2012268970 dated Aug. 27, 2015.
Official Action corresponding to Canadian Patent Application No. 2,837,804 dated May 1, 2015.
Official Action corresponding to Canadian Patent Application No. 2,778,871 dated Jan. 30, 2014.
Official Action corresponding to Chinese Patent Application No. 201080056911.6 dated Jul. 31, 2013.
Official Action corresponding to European Patent Application No. 00 944 034.8-2401 dated Oct. 7, 2004.
Official Action corresponding to Japanese Patent Application No. 2012-504036 dated Aug. 26, 2013.
Official Action corresponding to Japanese Patent Application No. 2012-542583 dated Apr. 22, 2014.
Official Action corresponding to Korean Patent Application No. 10-2011-7018847 dated Jan. 30, 2013.
Official Action corresponding to Russian Patent Application No. 2012114662/10(022146) dated Dec. 18, 2013.
Official Action corresponding to Russian Patent Application No. 2012114662/10(022146) dated Sep. 8, 2014.
Official Action corresponding to Russian Patent Application No. 2012115491 dated Dec. 23, 2013.
Official Action corresponding to U.S. Appl. No. 10/030,605 dated Apr. 12, 2006.
Official Action corresponding to U.S. Appl. No. 10/030,605 dated Aug. 10, 2005.
Official Action corresponding to U.S. Appl. No. 10/030,605 dated Feb. 15, 2005.
Official Action corresponding to U.S. Appl. No. 10/030,605 dated Feb. 28, 2007.
Official Action corresponding to U.S. Appl. No. 10/030,605 dated Jul. 1, 2008.
Official Action corresponding to U.S. Appl. No. 10/030,605 dated Nov. 16, 2007.
Official Action corresponding to U.S. Appl. No. 10/030,605 dated Sep. 21, 2004.
Official Action corresponding to U.S. Appl. No. 11/283,332 dated Jan. 9, 2008.
Official Action corresponding to U.S. Appl. No. 11/283,332 dated Mar. 3, 2010.
Official Action corresponding to U.S. Appl. No. 11/283,332 dated May 30, 2008.
Official Action corresponding to U.S. Appl. No. 11/283,332 dated Nov. 28, 2008.
Official Action corresponding to U.S. Appl. No. 11/283,332 dated Sep. 3, 2013.
Official Action corresponding to U.S. Appl. No. 11/283,332 dated Sep. 4, 2009.
Official Action corresponding to U.S. Appl. No. 11/656,646 dated May 25, 2010.
Official Action corresponding to U.S. Appl. No. 11/656,646 dated Nov. 13, 2009.
Official Action corresponding to U.S. Appl. No. 11/656,646 dated Sep. 1, 2009.
Official Action corresponding to U.S. Appl. No. 11/732,632 dated Aug. 21, 2009.
Official Action corresponding to U.S. Appl. No. 11/732,632 dated Jun. 3, 2009.
Official Action corresponding to U.S. Appl. No. 11/732,632 dated Mar. 19, 2010.
Official Action corresponding to U.S. Appl. No. 12/072,959 dated Aug. 30, 2013.
Official Action corresponding to U.S. Appl. No. 12/072,959 dated Jan. 27, 2009.
Official Action corresponding to U.S. Appl. No. 12/072,959 dated Jan. 5, 2010.
Official Action corresponding to U.S. Appl. No. 12/072,959 dated Jul. 24, 2008.
Official Action corresponding to U.S. Appl. No. 12/514,550 dated Aug. 3, 2011.
Official Action corresponding to U.S. Appl. No. 12/514,550 dated Mar. 12, 2012.
Official Action corresponding to U.S. Appl. No. 12/514,550 dated Sep. 15, 2011.
Official Action corresponding to U.S. Appl. No. 13/142,195 dated Feb. 11, 2013.
Official Action corresponding to U.S. Appl. No. 13/142,195 dated Feb. 4, 2014.
Official Action corresponding to U.S. Appl. No. 13/142,195 dated May 29, 2013.
Official Action corresponding to U.S. Appl. No. 13/144,809 dated Oct. 18, 2013.
Official Action corresponding to U.S. Appl. No. 13/516,002 dated Jan. 26, 2015.
Official Action corresponding to U.S. Appl. No. 13/516,002 dated Apr. 6, 2015.
Official Action corresponding to U.S. Appl. No. 14/126,341 dated May 1, 2015.
Ohashi et al., "Efficient protein selection based on ribosome display system with purified components," Biochemical and Biophysical Research Communications. vol. 352 pp. 270-276 (2007).
Pack, P., and Pluckthun, A., "Miniantibodies: Use of Amphipathic Helices to Produce Functional, Flexibly Linked Dimeric Fv Fragments with High Avidity in *Escherichia coli*," Biochemsitry. vol. 31, No. 6 pp. 1579-1584 (1992).
Raasi Shahri et al, Binding of polyubiquitin chains to ubiquitin-associated (UBA) domains of HHR23A, J. Mol. Biol., 2004, v. 341, p. 1367-1379.
Rahighi et al., "Specific Recognition of Linear Ubiquitin Chains by NEMO Is Important for NF-κB Activation," Cell. vol. 136 pp. 1098-1109 (2009).
Richardson et al., "Looking at proteins: representations, folding, packing, and design," Biophysical Journal. vol. 63 pp. 1186-1209 (1992).
Riddle et al., "Functional rapidly folding proteins from simplified amino acid sequences," Nature Structural Biology. vol. 4, No. 10 pp. 805-809 (1997).
Search Report corresponding to Chinese Patent Application No. 201080056911.6 dated Jun. 14, 2013.
Skerra, "Engineered protein scaffolds for molecular recognition," Journal of Molecular Recognition. vol. 13, No. 4 pp. 167-187 (2000).
Smith et al., "Small Binding Proteins Selected from a Conbinatorial Repertoire of Knottins Displayed on Phage," Journal of Molecular Biology. vol. 277, No. 2 pp. 317-332 (1998).

(56) References Cited

OTHER PUBLICATIONS

Skerra et al., "Alternative non-antibody scaffolds for molecular recognition," Current Opinion in Biotechnology, vol. 18, No. 4, pp. 295-304 (2007).

Wells, and Lowmann, "Rapid evolution of peptide and protein binding properties in vitro," Current Opinion in Biotechnology. vol. 3 pp. 355-362 (1992).

Wells, "Additivity of Mutational Effects in Proteins," Biochemistry. vol. 29, No. 37 pp. 8509-8517 (1990).

Yeh et al., "Ubiquitin-like proteins: new wines in new bottles," Gene. vol. 248, Nos. 1-2 pp. 1-14 (2000).

Zahnd et al., "Ribosome display: selecting and evolving proteins in vitro that specifically bind to a target," Nature Methods. vol. 4, No. 3 pp. 269-279 (2007).

Zhang et al., "Directed evolution of a fucosidase from a galactosidase by DNA shuffling and screening," PNAS. vol. 94 pp. 4504-4509 (1997).

Official Action corresponding to U.S. Appl. No. 14/126,341 dated Sep. 29, 2015.

\* cited by examiner

```
 1 mqifvytdtgktitlevepsdtienvkakiqdkegippdcqrlliwagkqledgrtlsdynidvaeylgiswmpalhlvlrlrgg---------gig
85 mqifvatdtgktitlevepsdtienvkakiqdkegippdcqrlliwagkqledgrtlsdynirdtvslhlvlrlraa
```

FIG. 1b.

```
 1 mqifvytdtgktitlevepsdtienvkakiqdkegippdcqrlliwagkqledgrtlsdynidvaeylgiswmpalhlvlrlraa---------gig
85 mqifvltstgktitlevepsdtienvkakiqdkegippdcqrlliwagkqledgrtlsdynitrnyhlhlvlrlraa
```

FIG. 1c.

```
 1 mqifvytdtgktitlevepsdtienvkakiqdkegippdcqrlliwagkqledgrtlsdynidvaeylgiswmpalhlvlrlraa         gig
85 mqifvlrtgktitlevepsdtienvkakiqdkegippdcqrlliwagkqledgrtlsdynitskgslhlvlrlraa
```

FIG. 1d.

```
 1 mqifvytdtgktitlevepsdtienvkakiqdkegippdcqrlliwagkqledgrtlsdynidvaeylgiswmpalhlvlrlraa---------gig
85 mqifv-trtgktitlevepsdtienvkakiqdkegippdcqrlliwagkqledgrtlsdyniqnfqlhlvlrlraa
```

FIG. 1e.

```
 1 mqifvytdtgktitlevepsdtienvkakiqdkegippdcqrlliwagkqledgrtlsdynidvaeylgiswmpalhlvlrlraa---------gig
85 mqifvdketgktitlevepsdtienvkakiqdkegippdcqrlliwagkqledgrtlsdynieqlnwlhlvlrlraa
```

FIG. 1f.

```
 1 mqifvytdtgktitlevepsdtienvkakiqdkegippdcqrlliwagkqledgrtlsdynidvaeylgiswmpalhlvlrlraa---------gig
85 mqifvatdtgktitlevepsdtienvkakiqdkegippdcqrlliwagkqldgrtlsdynihdesalhlvlrlraa
```

FIG. 1g.

```
 1 mqifvytdtgktitlevepsdtienvkakiqdkegippdcqrlliwaskqledgrtlsdynidvaeylgiswmpalhlvlrlraa---------gig
85 mqifvstftgktitlevepsdtienvkakiqdkegippdcqrlliwagkqledgrtlsdynlidwsqlhlvlrlraa
```

FIG. 1h.

```
 1 mqifvytdtgktitlevepsdtienvkakiqdkegippdcqrlliwagkqledgrtlsdynidvaeylgiswmpalhlvlrlraa---------gig
85 mqifvstrtgktitlevepsdtienvkakiqdkegippdcqrlliwagkqledgrtlsdynirknytlhlvlrlraa
```

FIG. 1i.

```
 1 mqifvytdtgktitlevepsdtienvkakiqdkegippdcqrlliwageqledgrtlsdynidvaeylgiswmpalhlvlrlraa---------gig
85 mrifvytatgktitlevepsdtienvkakiqdkegippdcqrlliwagkqledgrtlsdynisekkklhlvlrlraa
```

FIG. 1j.

```
  mqifvxtxxgktitlevepsdtienvkakiqdkegippdqqrlliwagkqledgrtlsdynixxxxxxxxxxxxxlhlvlrlrnn (linker)
  mqifvxtxxgktitlevepsdtienvkakiqdkegippdqqrlliwagkqledgrtlsdynixxxxxlhlvlrlraa
```

FIGUR 3

SEQUENCE LISTING

<160> NUMBER OF SEQ ID NOS: 18

<210> SEQ ID NO 1
<211> LENGTH: 76
<212> TYPE: PRT
<213> ORGANISM: Artificial sequence
<220> FEATURE:
<223> OTHER INFORMATION: Artificially synthesized ubiquitin

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2

```
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 40401

<400> SEQUENCE: 2

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Val Ala
    50                  55                  60

Glu Tyr Leu Gly Ile Ser Trp Met Pro Ala Leu His Leu Val Leu Arg
65                  70                  75                  80

Leu Arg Gly Gly Ile Gly Met Gln Ile Phe Val Ala Thr Asp Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
        115                 120                 125

Arg Leu Ile Trp Ala Gly Lys Gln Leu Glu Asp Gly Arg Thr Leu Ser
    130                 135                 140

Asp Tyr Asn Ile Arg Asp Thr Val Ser Leu His Leu Val Leu Arg Leu
145                 150                 155                 160

Arg Ala Ala

<210> SEQ ID NO 3
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 59517

<400> SEQUENCE: 3

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Val Ala
    50                  55                  60

Glu Tyr Leu Gly Ile Ser Trp Met Pro Ala Leu His Leu Val Leu Arg
65                  70                  75                  80

Leu Arg Ala Ala Gly Ile Gly Met Gln Ile Phe Val Leu Thr Ser Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
        115                 120                 125

Arg Leu Ile Trp Ala Gly Lys Gln Leu Glu Asp Gly Arg Thr Leu Ser
    130                 135                 140
```

Asp Tyr Asn Ile Thr Arg Asn Tyr His Leu His Leu Val Leu Arg Leu
145                 150                 155                 160

Arg Ala Ala

<210> SEQ ID NO 4
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 59649

<400> SEQUENCE: 4

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Val Ala
    50                  55                  60

Glu Tyr Leu Gly Ile Ser Trp Met Pro Ala Leu His Leu Val Leu Arg
65                  70                  75                  80

Leu Arg Ala Ala Gly Ile Gly Met Gln Ile Phe Val Leu Thr Arg Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
        115                 120                 125

Arg Leu Ile Trp Ala Gly Lys Gln Leu Glu Asp Gly Arg Thr Leu Ser
    130                 135                 140

Asp Tyr Asn Ile Thr Ser Lys Ser Ser Leu His Leu Val Leu Arg Leu
145                 150                 155                 160

Arg Ala Ala

<210> SEQ ID NO 5
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 60423

<400> SEQUENCE: 5

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Val Ala
    50                  55                  60

Glu Tyr Leu Gly Ile Ser Trp Met Pro Ala Leu His Leu Val Leu Arg
65                  70                  75                  80

Leu Arg Ala Ala Gly Ile Gly Met Gln Ile Phe Val Arg Thr Arg Thr
                85                  90                  95

Gly Lys Thr Ile Thr Leu Glu Val Glu Pro Ser Asp Thr Ile Glu Asn
            100                 105                 110

```
Val Lys Ala Lys Ile Gln Asp Lys Glu Gly Ile Pro Pro Asp Gln Gln
            115                 120                 125

Arg Leu Ile Trp Ala Gly Lys Gln Leu Glu Asp Gly Arg Thr Leu Ser
        130                 135                 140

Asp Tyr Asn Ile Gln Asn Gln Phe Gln Leu His Leu Val Leu Arg Leu
145                 150                 155                 160

Arg Ala Ala

<210> SEQ ID NO 6
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 60323

<400> SEQUENCE: 6

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Val Ala
    50                  55                  60

Glu Tyr Leu Gly Ile Ser Trp Met Pro Ala Leu His Leu Val Leu Arg
65                  70                  75                  80

Leu Arg Ala Ala Gly Ile Gly Met Gln Ile Phe Val Asp Thr Glu Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
            115                 120                 125

Arg Leu Ile Trp Ala Gly Lys Gln Leu Glu Asp Gly Arg Thr Leu Ser
        130                 135                 140

Asp Tyr Asn Ile Glu Gln Leu Asn Trp Leu His Leu Val Leu Arg Leu
145                 150                 155                 160

Arg Ala Ala

<210> SEQ ID NO 7
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 60397

<400> SEQUENCE: 7

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Asp Val Ala
    50                  55                  60
```

Glu Tyr Leu Gly Ile Ser Trp Met Pro Ala Leu His Leu Val Leu Arg
65                  70                  75                  80

Leu Arg Ala Ala Gly Ile Gly Met Gln Ile Phe Val Ala Thr Asp Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
        115                 120                 125

Arg Leu Ile Trp Ala Gly Lys Gln Leu Lys Asp Gly Arg Thr Leu Ser
    130                 135                 140

Asp Tyr Asn Ile Asn Asp Glu Ser Ala Leu His Leu Val Leu Arg Leu
145                 150                 155                 160

Arg Ala Ala

<210> SEQ ID NO 8
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 59507

<400> SEQUENCE: 8

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Ser Lys
        35                  40                  45

Gln Leu Glu Asp Gly Arg Thr Leu Ser Asp Tyr Asn Ile Asp Val Ala
    50                  55                  60

Glu Tyr Leu Gly Ile Ser Trp Met Pro Ala Leu His Leu Val Leu Arg
65                  70                  75                  80

Leu Arg Ala Ala Gly Ile Gly Met Gln Ile Phe Val Ser Thr Phe Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
        115                 120                 125

Arg Leu Ile Trp Ala Gly Lys Gln Leu Glu Asp Gly Arg Thr Leu Ser
    130                 135                 140

Asp Tyr Asn Ile Ile Asp Trp Ser Gln Leu His Leu Val Leu Arg Leu
145                 150                 155                 160

Arg Ala Ala

<210> SEQ ID NO 9
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 59987

<400> SEQUENCE: 9

Met Gln Ile Phe Val Tyr Thr Asp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Asp Val Ala
 50                  55                  60

Glu Tyr Leu Gly Ile Ser Trp Met Pro Ala Leu His Leu Val Leu Arg
 65                  70                  75                  80

Leu Arg Ala Ala Gly Ile Gly Met Gln Ile Phe Val Ser Thr Arg Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
            115                 120                 125

Arg Leu Ile Trp Ala Gly Lys Gln Leu Glu Asp Gly Arg Thr Leu Ser
    130                 135                 140

Asp Tyr Asn Ile Arg Lys His Tyr Thr Leu His Leu Val Leu Arg Leu
145                 150                 155                 160

Arg Ala Ala

<210> SEQ ID NO 10
<211> LENGTH: 163
<212> TYPE: PRT
<213> ORGANISM: Artificial sequence
<220> FEATURE:
<223> OTHER INFORMATION: Artificially synthesized dimeric ubiquitin
      binding protein 59603

<400> SEQUENCE: 10

Met Gln Ile Phe Val Tyr Thr Asp Thr Gly Lys Thr Ile Thr Leu Glu
 1                   5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Glu
            35                  40                  45

Gln Leu Glu Asp Gly Arg Thr Leu Ser Asp Tyr Asn Ile Asp Val Ala
 50                  55                  60

Glu Tyr Leu Gly Ile Ser Trp Met Pro Ala Leu His Leu Val Leu Arg
 65                  70                  75                  80

Leu Arg Ala Ala Gly Ile Gly Met Arg Ile Phe Val Tyr Thr Ala Thr
                85                  90                  95

Gly Lys Thr Ile Thr Leu Glu Val Glu Pro Ser Asp Thr Ile Glu Asn
            100                 105                 110

Val Lys Ala Lys Ile Gln Asp Lys Glu Gly Ile Pro Pro Asp Gln Gln
            115                 120                 125

Arg Leu Ile Trp Ala Gly Lys Gln Leu Glu Asp Gly Arg Thr Leu Ser
    130                 135                 140

Asp Tyr Asn Ile Ser Glu Lys Lys Leu His Leu Val Leu Arg Leu
145                 150                 155                 160

Arg Ala Ala

<210> SEQ ID NO 11
<211> LENGTH: 160
<212> TYPE: PRT
<213> ORGANISM: Artificial sequence
<220> FEATURE:
<223> OTHER INFORMATION: Artificially synthesized dimeric ubiquitin
      protein sequence
<220> FEATURE:

```
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (62)..(74)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (146)..(150)
<223> OTHER INFORMATION: Xaa can be any naturally occurring amino acid

<400> SEQUENCE: 11

Met Gln Ile Phe Val Xaa Thr Xaa Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Xaa Xaa Xaa
    50                  55                  60

Xaa Xaa Xaa Xaa Xaa Xaa Xaa Xaa Xaa Leu His Leu Val Leu Arg
65                  70                  75                  80

Leu Arg Asn Asn Met Gln Ile Phe Val Xaa Thr Xaa Thr Gly Lys Thr
                85                  90                  95

Ile Thr Leu Glu Val Glu Pro Ser Asp Thr Ile Glu Asn Val Lys Ala
            100                 105                 110

Lys Ile Gln Asp Lys Glu Gly Ile Pro Pro Asp Gln Gln Arg Leu Ile
        115                 120                 125

Trp Ala Gly Lys Gln Leu Glu Asp Gly Arg Thr Leu Ser Asp Tyr Asn
    130                 135                 140

Ile Xaa Xaa Xaa Xaa Xaa Leu His Leu Val Leu Arg Leu Arg Ala Ala
145                 150                 155                 160

<210> SEQ ID NO 12
<211> LENGTH: 8
<212> TYPE: PRT
<213> ORGANISM: Artificial sequence
<220> FEATURE:
<223> OTHER INFORMATION: Artificially synthesized insert

<400> SEQUENCE: 12

Asp Val Ala Glu Tyr Leu Gly Ile
1               5

<210> SEQ ID NO 13
<211> LENGTH: 232
<212> TYPE: PRT
<213> ORGANISM: Homo sapiens

<400> SEQUENCE: 13

Met Asn Phe Leu Leu Ser Trp Val His Trp Ser Leu Ala Leu Leu Leu
1               5                   10                  15
```

```
Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
65                   70                  75                  80

Met Arg Cys Gly Gly Cys Cys Asn Asp Glu Gly Leu Glu Cys Val Pro
             85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 14
<211> LENGTH: 3
<212> TYPE: PRT
<213> ORGANISM: Artificial sequence
<220> FEATURE:
<223> OTHER INFORMATION: Artificially synthesized linker

<400> SEQUENCE: 14

Gly Ile Gly
1

<210> SEQ ID NO 15
<211> LENGTH: 5
<212> TYPE: PRT
<213> ORGANISM: Artificial sequence
<220> FEATURE:
<223> OTHER INFORMATION: Artificially synthesized linker

<400> SEQUENCE: 15

Ser Gly Gly Gly Gly
1               5

<210> SEQ ID NO 16
<211> LENGTH: 7
<212> TYPE: PRT
<213> ORGANISM: Artificial sequence
<220> FEATURE:
<223> OTHER INFORMATION: Artificially synthesized linker

<400> SEQUENCE: 16
```

```
Ser Gly Gly Gly Gly Ile Gly
1               5

<210> SEQ ID NO 17
<211> LENGTH: 12
<212> TYPE: PRT
<213> ORGANISM: Artificial sequence
<220> FEATURE:
<223> OTHER INFORMATION: Artificially synthesized linker

<400> SEQUENCE: 17

Ser Gly Gly Gly Gly Ser Gly Gly Gly Gly Ile Gly
1               5                   10

<210> SEQ ID NO 18
<211> LENGTH: 10
<212> TYPE: PRT
<213> ORGANISM: Artificial sequence
<220> FEATURE:
<223> OTHER INFORMATION: Artificially synthesized linker

<400> SEQUENCE: 18

Ser Gly Gly Gly Gly Ser Gly Gly Gly Gly
1               5                   10
```

DIMERIC BINDING PROTEINS BASED ON MODIFIED UBIQUITINS

FIELD OF THE INVENTION

The invention relates to novel scaffolds with high affinity binding properties to targets due to modifications extending the binding site. The present invention relates to dimeric modified ubiquitin-based proteins with high binding capability to non-natural target proteins of human ubiquitin. Furthermore, the invention refers to fusion proteins or conjugates comprising said dimeric binding protein and diagnostically or therapeutically active components. The invention also relates to a multimer of dimeric modified ubiquitins and to multimers of fusion proteins or conjugates thereof and to pharmaceutical compositions containing these multimers.

In further embodiments, the invention is directed to polynucleotides coding for said novel binding protein or fusion protein or conjugate, vectors comprising said polynucleotide and host cells comprising said protein, fusion protein, conjugate, multimer and/or polynucleotide. In a preferred embodiment, said dimeric binding protein or fusion protein or multimer is included in a medicament or a diagnostic agent. Additionally, methods for producing said recombinant protein or fusion protein or conjugate or multimer as well as use of said proteins in medical treatment or in diagnostic methods are described.

BACKGROUND OF THE INVENTION

There is a growing demand for binding molecules consisting of amino acids which are not immunoglobulins. While until now antibodies represent the best-established class of binding molecules there is still a need for new binding molecules in order to target ligands with high affinity and specificity since immunoglobulin molecules suffer from major drawbacks. Although they can be produced quite easily and may be directed to almost any target, they have a quite complex molecular structure. There is an ongoing need to substitute antibodies by smaller molecules which can be handled in an easy way. These alternative binding agents can be beneficially used for instance in the medical fields of diagnosis, prophylaxis and treatment of diseases.

Proteins having relatively defined 3-dimensional structures, commonly referred to as protein scaffolds, may be used as starting material for the design of said alternative binding agents. These scaffolds typically contain one or more regions which are amenable to specific or random sequence variation, and such sequence randomisation is often carried out to produce a library of proteins from which the specific binding molecules may be selected. Molecules with a smaller size than antibodies and a comparable or even better affinity towards a target antigen are expected to be superior to antibodies in terms of pharmacokinetic properties and immunogenicity.

For example, WO 04/106368 (Scil Proteins GmbH) describes the generation of artificial binding proteins on the basis of ubiquitin. Ubiquitin is a small, monomeric, and cytosolic protein which is highly conserved among Eucaryota. In the organism, it plays a crucial role in an enormous range of physiological processes and attachment of ubiquitin is the second-most common posttranslational modification following phosphorylation.

Ubiquitin is particularly characterized by beta sheets arranged in an antiparallel manner and subdivided into α and β segments. A characteristic of ubiquitin protein is an antiparallel beta sheet exposed to one surface of the protein onto the back side of which a α helix is packed which lies perpendicularly on top of it. This ubiquitin-like folding motif clearly distinguishes ubiquitin from other proteins.

TECHNICAL PROBLEMS UNDERLYING THE PRESENT INVENTION AND THEIR SOLUTION

Compared to antibodies or other alternative scaffolds, artificial binding proteins on the basis of ubiquitin proteins (also referred to as Affilin®, a registered trademark of Scil Proteins GmbH) have many advantages: high affinity and specificity, small size, high stability, and cost effective manufacturing. However, there is still a need to further develop those proteins in terms of new therapeutic approaches with high affinities. While WO 05/05730 generally describes the use of ubiquitin scaffolds in order to obtain artificial binding proteins, no solution is provided on dimeric ubiquitin proteins in order to obtain a specific and high affinity binding to protein targets. There is still a strong need in the art for the generation of novel binding proteins using alternative ubiquitin scaffolds. Such novel binding proteins have the potential as effective therapeutics in medicine.

There remains a strong need in the art for efficient medical therapeutics. Ideally, innovative therapeutics in which the binding protein does not have the disadvantages of commonly used antibodies should be efficient. In order to achieve this, the disease target should be highly specific for a certain disease and binding to such target should occur with high affinity and selectivity. Therefore, it is an object of the present invention to provide alternative scaffold proteins based on modified ubiquitin having high binding specificities for a given non-natural target proteins. Thus, it is an object of the invention to provide binding proteins that are advantageous as compared to antibodies.

The object of the present invention is to provide alternative ubiquitin-based binding proteins with high binding specificities for non-natural target proteins of human ubiquitin. The problem is solved by extending the binding site for such target proteins. The solution to this problem is to insert structures in the modified ubiquitin protein that allow for an extended binding site. The structures described by the embodiments of claim 1 allow the formation of an extended structure, optionally a loop, thereby evolving new functionalities, for example by forming an extending binding site for non-natural targets, while preserving the overall structure and function of the ubiquitin scaffold.

Still further objects are the provision of methods on how to obtain said binding proteins, uses of these novel binding proteins as well as fusion proteins and conjugates comprising said novel binding proteins.

The above-described objects are solved and the advantages are achieved by the subject-matter of the enclosed independent claims. Preferred embodiments of the invention are included in the dependent claims as well as in the following description, examples and figures. The above overview does not necessarily describe all problems solved by the present invention.

SUMMARY OF THE INVENTION

In a first aspect, the invention provides a hetero-dimeric modified ubiquitin protein with binding capability to a non-natural target protein of human ubiquitin, comprising two ubiquitin monomers linked together in a head-to-tail arrangement,
wherein both monomers of said hetero-dimeric protein are differently modified at least by substitutions of at least 5, 6, 7, or 8 amino acids corresponding to positions 2, 4, 6, 8, 62, 63, 64, 65, 66, and 68 of SEQ ID NO: 1, and
wherein 2-15 amino acids are inserted in at least one ubiquitin monomer 0, 1, 2, or 3 amino acids distant from said amino acid substitutions corresponding to positions 2, 4, 6, 8, 62, 63, 64, 65, 66, and 68 of SEQ ID NO:1, and
wherein said modified ubiquitin monomers have an amino acid identity to SEQ ID NO: 1 of at least 75% or at least 85% and said modified hetero-dimeric ubiquitin have a specific detectable binding affinity to said non-natural target protein of Kd=$10^{-7}$-$10^{-12}$ M.

In a second aspect the present invention relates to a fusion protein or a conjugate comprising a hetero-dimeric modified ubiquitin protein according to the first aspect fused with or conjugated to a pharmaceutically or diagnostically active component, wherein said pharmaceutically active component is optionally a cytokine, a chemokine, a cytotoxic compound, a ubiquitin based binding protein or an enzyme, or wherein said diagnostically active component is selected from a fluorescent compound, a photosensitizer, or a radionuclide.

In a third aspect the present invention relates to a multimer of a hetero-dimeric modified ubiquitin protein according to the first aspect or a fusion protein or conjugate thereof according to the second aspect.

In a fourth aspect the present invention relates to a pharmaceutical composition containing a hetero-dimeric modified ubiquitin protein according to the first aspect or a modified ubiquitin fusion protein or a conjugate according to the second aspect or a multimer according to the third aspect or a combination thereof and a pharmaceutically acceptable carrier.

In a fifth aspect the present invention relates a diagnostic agent comprising a hetero-dimeric modified ubiquitin protein according to the first aspect or a modified ubiquitin fusion protein or a conjugate according to the second aspect or a multimer according to the third aspect with a diagnostically acceptable carrier.

In a sixth aspect the present invention relates to a polynucleotide encoding the protein as according to the first aspect or a modified ubiquitin fusion protein or a conjugate according to the second aspect or a multimer according to the third aspect.

In a seventh aspect the present invention relates to a vector comprising the polynucleotide of the sixth aspect.

In a eighth aspect the present invention relates to a host cell the protein as according to the first aspect or a modified ubiquitin fusion protein or a conjugate according to the second aspect or or a multimer according to the third aspect or a polynucleotide as defined in the sixth aspect; or a vector as defined in the seventh aspect.

In an ninth aspect the present invention relates to a method for the generation of a hetero-dimeric modified ubiquitin protein according to the first aspect comprising the following steps:
a) providing an ubiquitin;
b) providing a non-natural ligand protein of ubiquitin as potential target;
c) modifying said ubiquitin in order to obtain a ubiquitin monomer having an amino acid sequence identity to the amino acid sequence of SEQ ID NO: 1 of at least 75%, wherein 5, 6, 7, or 8 amino acids are modified at least by substitution of amino acids corresponding to and selected from positions 2, 4, 6, 8, 62, 63, 64, 65, 66, and/or 68, wherein 2-15 amino acids are inserted 0, 1, 2, or 3 amino acids distant from said amino acid substitutions corresponding to and selected from positions 2, 4, 6, 8, 62, 63, 64, 65, 66, and 68 of SEQ ID NO:1, optionally
d) linking two of said differently modified ubiquitin monomers;
e) contacting said hetero-dimeric modified ubiquitin with said target protein;
f) identifying modified hetero-dimeric modified ubiquitin which bind to said target protein with a specific binding affinity of $10^{-7}$-$10^{-12}$M, and optionally
g) isolating said dimeric modified ubiquitin proteins.

In a tenth aspect the present invention relates to a protein according to the first aspect, a fusion protein or conjugate according to the second aspect, or a multimer according to the third aspect for use in a method of medical treatment or diagnosis.

This summary of the invention does not necessarily describe all features of the present invention. Other embodiments will become apparent from a review of the ensuing detailed description.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs. Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland). All sequences referred to herein are disclosed in the attached sequence listing that, with its whole content and disclosure, is a part of this specification.

Modified Ubiquitin Proteins as Binding Proteins

The term "ubiquitin protein" covers the ubiquitin in accordance with SEQ ID NO: 1 and modifications thereof according to the following definition. Ubiquitin is highly conserved in eukaryotic organisms. For example, in all mammals investigated up to now ubiquitin has the identical amino acid sequence. Particularly preferred are ubiquitin molecules from humans, rodents, pigs, and primates. Additionally, ubiquitin from any other eukaryotic source can be used. For instance ubiquitin of yeast differs only in three amino acids from the wild-type human ubiquitin. Generally, the unmodified monomeric ubiquitin proteins covered by said term "ubiquitin protein" show an amino acid identity of more than 70%, preferably more than 75% or more than 80%, of more than 85%, of more than 90%, of more than 95%, of more than 96% or up to a sequence identity of 97% to SEQ ID NO: 1.

In order to cover embodiments wherein the modifications are introduced into a ubiquitin protein which is not identical but similar to SEQ ID NO: 1, the term "corresponding to" has been used. In said not identical but similar ubiquitins the positions of amino acids specified herein might be different to SEQ ID NO: 1; nevertheless they can be allocated to those positions which are designated by the positions referring to SEQ ID NO: 1. "Not identical to but similar" describes e.g. ubiquitins which are of non-human origin or which are derived from SEQ ID NO: 1 and differ therefore in their amino acid sequence to. SEQ ID NO: 1.

The polypeptide chain of ubiquitin consists of 76 amino acids (SEQ ID NO: 1) and corresponding to a monomer and is folded in an extraordinary compact α/β structure (Vijay-Kumar, 1987): almost 87% of the polypeptide chain is involved in the formation of the secondary structural elements by means of hydrogen bonds. Secondary structures are three and a half alpha-helical turns as well as an antiparallel β sheet consisting of four strands. The characteristic arrangement of these elements is generally considered as so-called ubiquitin-like folding motif. A further structural feature is a marked hydrophobic region in the protein interior between the alpha helix and the β sheet.

The amino acids of the four beta strands which contribute to the formation of the antiparallel beta sheet are according to the invention and according to the structure 1UBQ in the following amino acid positions of SEQ ID NO: 1: First strand (amino-terminal): 2 to 7; second beta sheet strand: 12 to 16; third strand: 41 to 45; fourth strand carboxy-terminal): 65 to 71. The position of the strands if the sheet is viewed from the top (amino terminus at the bottom, carboxy terminus on top) from left to right is: 2nd, 1st, 4th, 3rd strand wherein the polypeptide chain between the 1st and 4th strand forms the alpha helix.

The term "a modified ubiquitin protein" refers to modifications of the ubiquitin protein of any one of substitutions, insertions or deletions of amino acids or a combination thereof while substitutions are the most preferred modifications which may be supplemented by any one of the modifications described above. The number of modifications is strictly limited as each of said modified monomeric ubiquitin units has an amino acid identity to SEQ ID NO: 1 of at least one of the group of 75%, at least 83%, at least 85%%, at least 87% and at least 90%. At the most, the overall number of substitutions in a monomeric unit related to a novel binding property to a non-natural target is, therefore, limited to 16 amino acids corresponding to 80% amino acid identity taking into account only substitutions and deletions. If the insertions are included in the calculation of the total amino acid identity, said identity to SEQ ID NO: 1 may be between 75% and 80%. The total number of substituted or deleted amino acids in the dimeric ubiquitin molecule may be up to 32 amino acids. This is corresponding to about 20% amino acids that are substituted based on the unmodified dimeric ubiquitin protein. The amino acid identity of the dimeric modified ubiquitin protein compared to a dimeric unmodified ubiquitin protein with a basic monomeric sequence of SEQ ID NO: 1 is selected from at least one of the group of at least 75%, at least 80%, at least 83%, at least 85%%, at least 86%, at least 87%, at least 88%, at least 89% and at least 90%.

The term "loop" or "loop region" refers to regions of non-repetitive conformations connecting regular secondary structure elements such as alpha-helix or beta-strands of ubiquitin. The structure of human ubiquitin reveals 7 reverse turns (loops) which connect secondary structure elements: 7-11, 18-21, 37-40, 45-48, 51-54, 57-60, 62-65 (Vijay-Kumar et al. 1987 J Mol Biol.; 194(3):531-44).

The term "insertions" comprises the addition of amino acids to the original amino acid sequence of a protein. In this invention, the additional amino acids to a ubiquitin monomer are described wherein the ubiquitin remains stable without significant structural change.

Location of the Insertion in the Dimeric Ubiquitin

Said monomeric ubiquitin units (ubiquitin monomers) contain an insertion in one or in both ubiquitin monomers, preferably in one monomer. It is also possible that the two ubiquitin monomers contain each identical or different insertions. In a still further embodiment, two or three or four insertions are included in one or in both ubiquitin monomers.

Size of the Insertion

The invention covers insertions of 2 to 15 amino acids preferably in the binding region of the ubiquitin monomer(s) that defines the binding to a non-natural target. Specifically, the number of amino acids to be inserted is 2, 3, 4, 5, 6, 7, 8, 9, 10, 11, 12, 13, 14, or 15. One embodiment of the invention shows an insert of 8 amino acids of the first ubiquitin monomer (e.g. see SEQ ID NO: 12). The total number of amino acids of all insertions is however limited by maintaining the structural integrity of the modified ubiquitin and its binding capability to a non-natural target protein. The insertion may comprise 6-10 amino acids or 7-9 amino acids or 8 amino acids in one or both monomeric ubiquitin proteins or any other number (2, 3, 4, 5, 6, 7, 8, 9, 10, 11, 12, 13, 14, 15) of amino acid insertions covered by the range of 2 to 15 amino acids. At the most insertions of 15 amino acids may be tolerated by an monomeric ubiquitin, preferably 6-10 amino acids, most preferred 8 amino acids. An insertion of 8 amino acids in the region of residues 61 to 65, between amino acids corresponding to amino acid positions 61-62 or positions 62-63 or positions 63-64 or positions 64-65 of SEQ ID NO: 1, most preferred between amino acids corresponding to positions 61-62 of SEQ ID NO: 1 or closely adjacent (1-3 amino acids) to said substituted amino acids or 0, 1, 2, 3, 4, or 5 amino acids distant from beta sheets, is most preferred. An insertion of 6 to 10 (6, 7, 8, 9, or 10) amino acids, preferably 8 amino acids, is extending the natural loop region and thereby extending the binding site for targets which is beneficial for the binding interaction between the target and the modified ubiquitin (Affilin®).

Location of the Insertion in the Monomeric Ubiquitin

It is further preferred that the insertion of amino acids is closely adjacent, optionally 0, 1, 2, 3, 4, or 5 amino acids, distant from beta sheet strands, preferably distant from the fourth (C-terminal) or the first (N-terminal) beta-strand, optionally wherein said insertion is located in the N-terminal (first) ubiquitin monomer. The insertion is generally not located in a beta sheet but adjacent to beta sheets, optionally 0, 1, 2, 3, 4, or 5 amino acids, distant from beta sheets thereby forming an extended structure close to substituted amino acids in beta sheets. It is preferred that the insertion is 0, 1, 2, 3, 4, or 5 amino acids distant from the fourth (C-terminal) or the first (N-terminal) beta-strand.

The insertion is preferred within or in close proximity of 1 to 3 amino acids in direction of the N- or C-terminus of said amino acid substitutions. A preferred insertion of amino acids is in one loop region of said modified monomeric ubiquitin. A loop region in ubiquitin refers to residues 7-11, 18-21, 37-40, 45-48, 51-54, 57-60, 62-65 of SEQ ID NO: 1, as further defined below. In one preferred embodiment of the invention, an insertion of additional amino acids is before (between positions 61 and 62) or within the loop region (amino acids 62 to 64) which is adjacent to the C-terminal beta sheet, thereby extending the existing loop region and forming a larger binding site. The addition of amino acids in natural surface-exposed loops of the ubiquitin protein is favourable in regions linking stable structural elements, such as beta-sheets. In one embodiment, the insertion is located in the loop region of residues 61 to 65, between amino acid residues corresponding to amino acids 61-62 or 62-63 or 63-64 or 64-65 of SEQ ID NO: 1, most preferred between amino acids corresponding to positions 61 and 62 of SEQ ID NO: 1. It is most preferred that an insertion of amino acids is C-terminal to substitutions of amino acids in the fourth beta-strand or in other words, that the insertion of amino acids is close to or within the loop region of amino acids 62 to 65. As it can be concluded from CD-spectra, the inserted sequence does not affect the global structure, but the insertion site does. Thus, the insertion of amino acids is preferred between amino acids corresponding to 61-62 or 62-63 or 63-64 or 64-65 of human ubiquitin of SEQ ID NO: 1, most preferred between amino acids corresponding to positions 61 and 62 of SEQ ID NO: 1. Such an insertion in the adjacent region to the fourth beta strand extends the natural loop region significantly, thereby forming an extended binding site for non-natural targets. The binding site is formed by substitutions within amino acids in the N-terminal region 2 to 8 and C-terminal region 62 to 68, along with an insertion of amino acids preferably in the loop region adjacent to the C-terminal region of modified amino acids. Substitutions and Insertions are preferred in amino acid regions 2 to 8 and 61 to 68. Most preferred are substitutions in region 2 to 8 of SEQ ID NO: 1 and a combination of substitutions and an insertion of 2 to 15 amino acids in at least one monomer of ubiquitin in amino acid region 61 to 68 of SEQ ID NO:1.

Advantages of the Insertions of Amino Acids

Preferably, there is only one insertion in one monomeric ubiquitin unit. Most preferred is an insertion in the N-terminal (first) monomeric ubiquitin unit of the dimer. Said insertion may participate in the newly generated binding of the modified ubiquitin to a non-natural target protein, for example to VEGF-A and its isoforms. A further positive effect of the insertion is an increase of the number of amino acids which may be substituted and may therefore participate in binding to the target. The insert may optionally form an extended structure, for example, a loop structure. The elongation of the ubiquitin structure by adding additional amino acids has no significant effects on the overall conformation and stability of the protein. The modified hetero-dimeric ubiquitin scaffold having substitutions and insertions remains soluble.

The invention provides for engineered, novel high affinity binding alternative scaffolds with extended interaction interface for non-natural targets. The formation of an extended or elongated structure, e.g. a loop structure, in close proximity to the substituted amino acids has several advantages. First, the target binding site is extended by the additional amino acids without disrupting the overall structure of the protein. The overall structure and function of the ubiquitin scaffold is preserved although supplementary amino acids are added to the protein. This results in binding to the non-natural targets with high affinity and specificity. Second, by forming an extended structure, the conformation might be changed in such a way that special targets or epitopes could be reached. The structural flexibility has the positive effect that the binding site is not fixed and therefore, the binding of targets to such a binding site formed by a combination of substituted amino acids and insertions is stronger. The binding would not be hindered by changes to the conformation of the target. The insertion site close to the C-terminal beta-sheet is thus more important for the binding to targets than the sequence of the insert itself. The insertion site is determining the target binding.

The term "substitution" comprises also the chemical modification of amino acids by e.g. substituting or adding chemical groups or residues to the original amino acid. The substitution of surface-exposed amino acids is crucial. In further embodiments of the invention at least 5, 6, 7, or 8 amino acids located in regions 2 to 8 and 62 to 68, particularly selected from positions 2, 4, 6, 8, 62, 63, 64, 65, 66 and/or 68 are modified by substitution and further 1 to 7 additional amino acids are modified by substitution, which substitutions are optionally selected from one or more of the amino acids in positions 36, 44, 70, 71, 72, and 73. It is to be understood that the present invention allows a combination of each of these variations in each monomeric unit (monomer), i.e. in the first and the second monomer. For instance the first monomer can comprise 5 modifications while the second unit comprises 6 or 7 modifications, the first monomer may comprise 7 modifications and the second unit 5 modifications etc. Each of the amino acids listed above can be selected in the first and/or second monomer which are then combined. Preferred substitutions and insertions are described herein below.

For determining the extent of sequence identity of a derivative of the ubiquitin to the amino acid sequence of SEQ ID NO: 1, for example, the SIM Local similarity program (Xiaoquin Huang and Webb Miller, "Advances in Applied Mathematics, vol. 12: 337-357, 1991) or Clustal, W. can be used (Thompson et al., Nucleic Acids Res., 22(22): 4673-4680, 1994.). The extent of the sequence identity of the modified protein to SEQ ID NO: 1 as defined herein is determined relative to the complete sequence of SEQ ID NO: 1. In the context of the present invention, the extent of sequence identity between a modified sequence and the sequence from which it is derived (also termed: "parent sequence") is generally calculated with respect to the total length of the unmodified sequence, if not explicitly stated otherwise.

Potential Binding Partners of the Dimeric Ubiquitin Proteins

In the present specification, the terms "target", "ligand" and "binding partner" are used synonymously and can be exchanged. When practicing the present invention, A preferred target, ligand and binding partner is a protein and more specifically an antigenic epitope present on proteins. A target, ligand and binding partner as understood in this invention is any protein capable of binding with an affinity as defined herein to the hetero-dimeric modified ubiquitin protein. The target or ligand or binding partner of the invention is a non-natural target for human ubiquitin or for ubiquitin dimers. This implies that the binding property is de novo generated and did not exist before creating hetero-dimeric modified ubiquitin binding proteins. In other words, the target of the invention cannot bind to an unmodified, wild-type ubiquitin.

Exemplary non-natural ligands of the dimeric modified ubiquitin proteins with insertion of 2 to 15 amino acids in at least one monomer might be for example, but by no means limited to, VEGF-A, ED-B, TNF-alpha, MIA-2, NGF, and IgG. The invention is not restricted to these specific ligands but can be performed on all or at least most of ligands and target molecules known in the art. Those targets can be selected by the skilled artisan within his general knowledge of the art. The following provides general definitions of ligands and targets and provides also selected examples of further potential binding partners.

The terms "protein capable of binding" or "binding protein" according to this invention refer to a hetero-dimeric modified ubiquitin protein comprising a binding domain to a target protein. Any such binding protein based on ubiquitin may comprise additional protein domains that are not binding domains, such as, for example, multimerization moieties, polypeptide tags, polypeptide linkers and/or non-proteinaceous polymer molecules. Some examples of non-proteinaceous polymer molecules are hydroxyethyl starch, polyethylene glycol, polypropylene glycol, or polyoxyalkylene. The binding to said target protein was de novo generated. Both ubiquitin monomers without the modifications (substitutions and insertions) cannot bind to the binding partner. Only after the modification, a new binding property was generated that did not exist before for native ubiquitin monomers. Only the artificial dimeric ubiquitin-structure with modifications binds to such non-natural targets.

While antibodies and fragments thereof are well known to the person skilled in the art, the binding protein of the invention is not an antibody or a fragment thereof, such as Fab or scFv fragments. Further, the binding domain of the invention does not comprise an immunoglobulin fold as present in antibodies. The binding proteins of the invention comprise only alternative scaffolds, in particular scaffolds based on modified ubiquitin-based dimeric proteins.

The term "VEGF-A" or briefly designated as "VEGF" comprises all proteins which show a sequence identity to SEQ ID NO: 13 (accession number P15692) of at least 70%, optionally 75%, further optionally 80%, 85%, 90%, 95%, 96% or 97% or more, or 100% and having the above defined functionality of VEGF. The term "VEGF-A" or briefly designated as "VEGF" also comprises isoforms of VEGF-A; well-known isoforms of VEGF-A are VEGF 121 and VEGF 165.

Ubiquitin Dimers

A "dimer" is considered as a protein in this invention which comprises two monomeric ubiquitin proteins (ubiquitin monomers). If the dimer comprises two differently modified monomers, it is called a "heteromeric-dimer" or "hetero-dimer". The "hetero-dimeric fusion protein" or "hetero-dimeric protein" of the invention is considered as a protein which comprises at least two differently modified monomeric ubiquitin proteins with binding regions providing together a specific binding property for a non-natural target as the specific binding partner. A hetero-dimer is accomplished by fusing two monomeric ubiquitin molecules wherein both of these molecules are differently modified as described herein. The "homo-dimeric fusion protein" or "homo-dimeric protein" of the invention is considered as a protein which comprises two identically modified monomeric ubiquitin proteins with binding regions. A homo-dimer is accomplished by fusing two monomeric ubiquitin molecules wherein both of these molecules are identically modified as described herein. Preferred are dimeric or tetrameric proteins or multimers thereof. Preferred binding regions are created by substitutions and insertion(s) in amino acid regions 2 to 8 and 62 to 68 of ubiquitin monomers. Most preferred are substitutions in region 2 to 8 of SEQ ID NO: 1 and a combination of substitutions and an insertion of 2 to 15 amino acids in at least one monomer of ubiquitin in amino acid region 61 to 68 of SEQ ID NO:1.

An advantage of dimerization, of differently or identically modified ubiquitin monomers in order to generate hetero- or homo-dimeric binding proteins with binding activity lies in the increase of the total number of amino acid residues that can be modified or in dimerization of a binding region to generate a new high affinity binding property to protein targets. The main advantage is that while even more amino acids are modified, the protein-chemical integrity is maintained without decreasing the overall stability of the ubiquitin scaffold of said newly created binding protein to non-natural protein targets. The total number of residues which can be modified in order to generate a novel binding site for a non-natural target is increased as the modified residues can be allocated to two monomeric modified ubiquitin proteins. The number of modifications can be both of SEQ ID NO: 1 multiplied and allotted to different monomeric molecules of ubiquitin corresponding to the number of modified monomeric ubiquitin molecules. A modular structure of the ubiquitin-based binding protein allows increasing the overall number of modified amino acids as said modified amino acids are included on said two monomeric ubiquitin molecules.

Thus, the use of the proteins of the invention having a binding site for the binding partner opens up the possibility to introduce an increased number of modified residues which do not unduly influence the protein-chemical integrity of the final binding molecule, since the overall amount of those modified residues is distributed over the two monomeric units (monomers) which form the dimer. Said dimeric modified ubiquitin proteins binding to a predefined target are present in a library of proteins. In one embodiment of the invention the monomeric proteins are fused to each other. The dimerized molecules can be used for further multimerization. The comments provided for dimerized ubiquitin molecules are mutatis mutandis also valid for higher multimerized molecules. Thus, the homo- or hetero-dimers binding to VEGF-A can be used for further multimerization. Thus, the dimeric protein can be further multimerised with the same dimeric protein or with a different dimeric protein. The different dimeric protein can have other specificities than the first dimeric protein. Preferred are dimeric or tetrameric proteins or multimers thereof. Examples are: A-A (Homo-Dimer), A-B (Hetero-Dimer), A-B-A-B, A-A-A-B, A-B-A-A, A-A-A-A, A-B-C-D, A-A-C-D. The constructs A-B-C-D and A-A-C-D can be bi-specific binding proteins with specificity for two different targets.

According to the invention, the two modified ubiquitin monomers which bind to one protein ligand are to be linked by head-to-tail fusion to each other using e.g. genetic methods. A "head to-tail fusion" is to be understood in this invention as fusing two proteins together by connecting them in the direction N-terminus to C-terminus. In this head-to-tail fusion, the ubiquitin monomers may be connected directly without any linker. Alternatively, the fusion of ubiquitin monomers can be performed via linkers, for example, a polypeptide linker.

As used herein, the term "linker" refers to a molecule that joins at least two other molecules either covalently or non-covalently, e.g., through hydrogen bonds, ionic or van der Waals interactions, e.g., a nucleic acid molecule that hybridizes to one complementary sequence at the 5' end and to another complementary sequence at the 3' end, thus joining two non-complementary sequences. A "linker" is to be understood in the context of the present application as a moiety that connects a first polypeptide with at least a further polypeptide. The second polypeptide may be the same as the first polypeptide or it may be different.

Preferred herein are peptide linkers. This means that the peptide linker is an amino acid sequence that connects a first polypeptide with a second polypeptide. In this invention, the peptide linker is an amino acid sequence which is able to link two ubiquitin monomers. Typically, a peptide linker has a length of between 1 and 20 amino acids; e.g. 1, 2, 3, 4, 5, 6, 7, 8, 9, 10, 11, 12, 13, 14, 15, 16, 17, 18, 19, or 20 amino acids. It is preferred that the amino sequence of the peptide linker is not immunogenic to human beings. An example of such linker is a glycine-serine-linker of variable length, for example, having at least the amino acid sequence GIG (SEQ ID NO: 14) or having at least the amino acid sequence SGGGG, for example GIG (SEQ ID NO: 14), SGGGG (SEQ ID NO: 15), SGGGGIG (SEQ ID NO: 16), SGGGGSGGGGIG (SEQ ID NO: 17) or SGGGGSGGGG (SEQ ID NO: 18) or (SGGG)n wherein n is any number between 1 to 4 The linkers may have a length between 2 and 16 amino acids. Also other linkers for the genetic fusion of two ubiquitin monomers are known in the art and can be used.

In one embodiment of the present invention, the two monomeric proteins are not linked together after having screened the most potent binding ubiquitin molecules but already the screening process is performed in the presence of the dimeric ubiquitins. After having received the sequence information on the most potent binding ubiquitin molecules, these molecules may be obtained by any other method, for example by chemical synthesis or by genetic engineering methods, e.g. by linking the two already identified monomeric ubiquitin units (ubiquitin monomers) together. The aforesaid also applies to homomers of the modified ubiquitin protein which provides a more efficient binding to a non-natural ligand protein.

Binding to Predefined Targets with High Specificity and Affinity by Specific Modifications It is thus an object of the present invention to provide novel dimeric proteins based on ubiquitin being able to bind specifically and with high affinity to predefined protein targets. Targets are selected that—under natural conditions—do not bind to ubiquitin ("non-natural targets") but can bind with high affinities to the novel modified dimeric ubiquitin-based protein. In one embodiment, the non-natural target is VEGF-A or its isoforms. However, the invention is not limited to VEGF-A or its isoforms. It is important that any other target could be used provided that the binding of the dimeric ubiquitin was de novo generated by the combination of substitutions and insertions. The dimeric ubiquitin proteins with a combination of substitutions and insertion in at least one monomer are engineered and artificial proteins with novel binding affinities to a target or ligand (which expressions are used herein interchangeably).

In one embodiment of the invention, modified novel binding proteins having an insertion in at least one monomer and substitutions bind to VEGF, preferably VEGF-A and isoforms as non-natural ligand protein. In humans, multiple spliced isoforms of VEGF-A have been identified. The most common isoforms are composed of 121, 165 and 189 amino acids, and the murine homologues lack one amino acid per isoform. The longer splice isoforms of VEGF-A, including VEGF165, contain a highly basic heparin-binding domain. However, modified ubiquitin binding proteins with insertions and substitutions could bind to any other non-natural target.

The substitution of amino acids for the generation of the novel binding domain specific to a given target, for example VEGF-A, can be performed according to the invention with any desired amino acid, i.e. for the modification to generate the novel binding property to a target, e.g. VEGF-A; it is not mandatory to take care that the amino acids have a particular chemical property or a side chain, respectively, which is similar to that of the amino acids substituted so that any generally amino acid desired can be used for this purpose provided it enhances the binding affinity to VEGF-A and does not deteriorate the structural integrity of the ubiquitin binding molecule.

In a further embodiment, the amino acid substitutions specifically defined herein are changed by other amino acids with similar chemical properties, so called "conservative substitutions", for example:
Ala, Val, Leu, Ile, Met, Pro, Phe, Trp: Amino acids with aliphatic hydrophobic side chains
Ser, Tyr, Asn, Gln, Cys: Amino acids with uncharged but polar side chains
Asp, Glu: Amino acids with acidic side chains
Lys, Arg, His: Amino acids with basic side chains
Gly: Neutral side chain The step of modification of the selected amino acids is performed according to the invention preferably by mutagenesis on the genetic level by random mutagenesis, i.e. a random substitution of the selected amino acids. Preferably, the modification of ubiquitin is carried out by means of methods of genetic engineering for the alteration of a DNA belonging to the respective protein. Preferably, expression of the ubiquitin protein is then carried out in prokaryotic or eukaryotic organisms.

In preferred embodiments, the amino acid residues are altered by the combination of amino acid substitutions and by insertions at least in one monomer. The number of amino acids which may be inserted is limited to 2 to 15 amino acids in a ubiquitin monomer, and accordingly 2, 3, 4, 5, 6, 7, 8, 9, 10, 11, 12, 13, 14, 15 amino acids with respect to the dimeric ubiquitin protein. In one embodiment, amino acid insertions are made in one monomeric subunit of the dimeric ubiquitin based binding protein, preferably in the N-terminal (first) monomeric subunit. Preferred positions for insertion are differently or identically modified and/or wherein 6-10 amino acids or 7-9 amino acids or 8 amino acids are inserted in one or both monomeric ubiquitin monomer. In one embodiment, insertion of amino acids is in one loop region of said modified monomeric ubiquitin or within or in close proximity of the amino acid substitutions specified in claim 1, optionally 0, 1, 2, or 3 amino acids in direction of the N- or C-terminus of the substituted positions specified in claim 1. In another embodiment, the insertion of amino acids is closely adjacent, optionally 0, 1, 2, 3, 4, or 5 amino acids, distant from beta sheet strands, preferably from the fourth (C-terminal) or the first (N-terminal) strand. Preferred are insertions in the N-terminal (first) monomer. Optional positions for insertion of amino acids are for example positions corresponding to human ubiquitin positions 61-62 or 62-63 or 63-64 or 64-65 which are closely adjacent to the substituted amino acid positions. Specifically the following positions for insertion of amino acids are chosen corresponding to human ubiquitin positions: 9-10 (1st beta-strand corresponding to amino acids 2-7), 35-36 (3rd beta-strand corresponding to amino acids 41-45), and most preferred before position 65 in close proximity to the $4^{th}$ beta-strand (4th beta-strand corresponding to amino acids 65-71).

Provided that e.g. non-human ubiquitin is used as starting protein (for example ubiquitin of yeast), the amino acid positions given for wild type human ubiquitin (SEQ ID NO: 1) have to be aligned with the modified ubiquitin in order to allot the corresponding proteins and amino acid positions to each other. The numbering (and alignment) of each of the monomeric ubiquitin subunits is done in the same way, i.e. an alignment of, for example, a dimer is started at amino acid position 1 for each respective subunit.

The modifications of a monomeric ubiquitin according to the invention used as building unit for a hetero-dimer accounts for in total up to about 25% of amino acids if the modifications comprise the combination of both substitutions and insertions. The modifications of a monomeric ubiquitin according to the invention used as building unit for a hetero-dimer accounts for in total up to about 15%, preferably 10%, of amino acids if the modifications comprise only substitutions. Considering this, there is a sequence identity to SEQ ID NO: 1 of the modified monomeric ubiquitin protein of at least 75% if modifications comprise substitutions and insertions. Considering this, there is a sequence identity to SEQ ID NO: 1 of the modified monomeric ubiquitin protein of at least 80%, at least 83%, at least 85%, at least 87% if modifications comprise only substitutions. In further embodiments of the invention, the sequence identity on amino acid level is at least 80%, at least 83%, at least 85%, at least 87% and furthermore at least 90% or at least 93% sequence identity to the amino acid sequence of SEQ ID NO: 1. If only substitutions are considered that are involved in generating a new binding to a target (and not substitutions related to biochemical properties, e.g. changes in Position 45, 75, 76) then the sequence identity on amino acid level is at least 88%, at least 91%, at least 92%, at least 93% to the amino acid sequence of SEQ ID NO: 1. If substitutions and insertions are considered that are involved in generating a new binding to a target (and not substitutions related to biochemical properties, e.g. changes in Position 45, 75, 76) then the sequence identity on amino acid level is at least 80% to the amino acid sequence of SEQ ID NO: 1. Thus, for example, in one embodiment, 7 amino acids are substituted and 8 amino acids are inserted to generate a new binding property, accounting to a sequence identity of at least 80% to SEQ ID NO: 1.

In a further embodiment of the invention, each of two ubiquitin monomers is substituted in 5 or 6 or 7 amino acids selected from regions 2-8 and 62-68, preferably selected from positions 6, 8, 62, 63, 64, 65, 66 of SEQ ID NO: 1 and additionally 2-15 amino acids are inserted at region 61-65, preferably in position 61-62 or 62-63 or 63-64 or 64-65 of the first (N-terminal) monomer, thus within close proximity to said substituted amino acids. Most preferred are substitutions in region 2 to 8 of SEQ ID NO: 1 and a combination of substitutions and an insertion of 2 to 15 amino acids in at least one monomer of ubiquitin in amino acid region 61 to 68 of SEQ ID NO:1. In another embodiment, the ubiquitin monomers to be modified in these positions were already pre-modified which does not influence the binding of targets. For example, further modifications could comprise substitutions at amino acids 75 and 76 or at amino acid 45 to generate better stability or protein-chemical properties. A modified ubiquitin monomer is obtainable wherein at least 5 amino acids, but in total up to 9, 10, 11, 12, 13, 14, 15 and a maximum of 16 amino acids, most preferred 5 to 9 amino acids, of the monomeric ubiquitin of SEQ ID NO: 1 are substituted. Additional 2 to 15 amino acids are inserted into the sequence. According to one embodiment, a modified monomeric ubiquitin could be obtained having 8 substitutions being involved in novel binding to a target and an insertion of 8 amino acids (for example, further 3 amino acids can be modified that does not affect the binding). Based on the total number of amino acids of ubiquitin this corresponds to a percentage of all modifications of about 26% (modifications involved in binding: about 22%). This was extraordinarily surprising and could not be expected since usually a much lower percentage is already sufficient to disturb the folding of the protein.

For the mutagenesis of surface exposed amino acids, these can be identified with respect to the available X-ray crystallographic structure. If no crystal structure is available attempts can be made by means of computer analysis to predict surface-exposed amino acids and the accessibility of individual amino acid positions with respect to the available primary structure or to model the 3D protein structure and to obtain information about potential surface-exposed amino acids in this manner. Further disclosure thereof can be taken e.g. from Vijay-Kumar et al. 1987 J. Mol. Biol. 194(3):531-44.

Surface exposed amino acid positions to be mutagenized, preferably substituted, are subjected to random mutagenesis and are afterwards re-integrated into the DNA coding for the protein from which they were removed previously. This is followed by a selection process for mutants with the desired binding properties. "Surface-exposed amino acids" are amino acids that are accessible to the surrounding solvent. If the accessibility of the amino acids in the protein is more than 8% compared to the accessibility of the amino acid in the model tripeptide Gly-X-Gly, the amino acids are called "surface-exposed". These protein regions or individual amino acid positions, respectively, are also preferred binding sites for potential binding partners for which a selection shall be carried out according to the invention. In addition, reference is made to Caster et al., 1983 Science, 221, 709-713, and Shrake & Rupley, 1973 J. Mol. Biol. 79(2): 351-371, which for complete disclosure are incorporated by reference in this application.

In another embodiment of the invention the amino acid positions to be mutagenized within these selected regions are identified. The amino acid positions selected in this way can then be mutagenized on the DNA level either by site-directed mutagenesis, i.e. a codon coding for a specific amino acid is substituted by a codon encoding another previously selected specific amino acid, or this substitution is carried out in the context of a random mutagenesis wherein the amino acid position to be substituted is defined but not the codon encoding the novel, not yet determined amino acid.

Variations of ubiquitin protein differing by amino acid substitutions or/and amino acid insertions in the region of the de novo generated artificial binding site from the parental protein and from each other can be generated by a targeted mutagenesis of the respective sequence segments. In this case, amino acids having certain properties such as polarity, charge, solubility, hydrophobicity or hydrophilicity can be replaced or substituted, respectively, by amino acids with respective other properties. Besides substitutions, the terms "mutagenesis" and "modified" and "replaced" comprise also insertions. On the protein level the modifications can also be carried out by chemical alteration of the amino acid side chains according to methods known to those skilled in the art.

Methods of Mutagenesis of Ubiquitin

As a starting point for the mutagenesis of the respective sequence segments, for example the cDNA of ubiquitin which can be prepared, altered, and amplified by methods known to those skilled in the art can be used. For site-specific alteration of ubiquitin in relatively small regions of the primary sequence (about 1-3 amino acids) commercially available reagents and methods are on hand ("Quik Change", Agilent; "Mutagene Phagemid in vitro Mutagenesis Kit", Bio-Rad). For the site-directed mutagenesis of larger regions specific embodiments of e.g. the polymerase chain reaction (PCR) are available to those skilled in the art. For this purpose a mixture of synthetic oligodeoxynucleotides having degenerated base pair compositions at the desired positions can be used for example for the introduction of the mutation. This can also be achieved by using base pair analogs which do not naturally occur in genomic DNA, such as e.g. inosine. Starting point for the mutagenesis of can be for example the cDNA of ubiquitin or also the genomic DNA. Furthermore, the gene coding for the ubiquitin protein can also be prepared synthetically.

Different methods known per se are available for mutagenesis comprising inter alia methods for site-specific mutagenesis, methods for random mutagenesis, mutagenesis using PCR or similar methods.

In a preferred embodiment of the invention the amino acid positions to be mutagenized are predetermined. The selection of amino acids to be modified is carried out to meet the limitations of present claim 1 with respect to those amino acids which have to be modified. In each case, a library of different mutants is generally established which is screened using methods known per se. Generally, a pre-selection of the amino acids to be modified can be particularly easily performed as sufficient structural information is available for the ubiquitin protein to be modified.

Methods for targeted mutagenesis as well as mutagenesis of longer sequence segments, for example by means of PCR, by chemical mutagenesis or using bacterial mutator strains also belong to the prior art and can be used according to the invention.

In one embodiment of the invention the mutagenesis is carried out by assembly of DNA oligonucleotides carrying the amino acid codon NNK. It should be understood, however, that also other codons (triplets) can be used. The mutations are performed in a way that the beta sheet structure is preferably maintained. Generally, the mutagenesis takes place on the outside of a stable beta sheet region exposed on the surface of the protein. It comprises both site-specific and random mutagenesis. Site-specific mutagenesis comprising a relatively small region in the primary structure (about 3-5 amino acids) can be generated with the commercially available kits of Agilent® (QuikChange®) or Bio-Rad® (Mutagene® phagemid in vitro mutagenesis kit) (cf. U.S. Pat. Nos. 5,789,166; 4,873,192).

If more extended regions are subjected to site-specific mutagenesis a DNA cassette must be prepared wherein the region to be mutagenized is obtained by the assembly of oligonucleotides containing the mutated and the unchanged positions (Nord et al., 1997 Nat. Biotechnol. 8, 772-777; McConell and Hoess, 1995 J. Mol. Biol. 250, 460-470.). Random mutagenesis can be introduced by propagation of the DNA in mutator strains or by PCR amplification (error-prone PCR) (e.g. Pannekoek et al., 1993 Gene 128, 135 140). For this purpose, a polymerase with an increased error rate is used. To enhance the degree of the mutagenesis introduced or to combine different mutations, respectively, the mutations in the PCR fragments can be combined by means of DNA shuffling (Stemmer, 1994 Nature 370, 389-391). A review of these mutagenesis strategies with respect to enzymes is provided in the review of Kuchner and Arnold (1997) TIBTECH 15, 523-530. To carry out this random mutagenesis in a selected DNA region also a DNA cassette must be constructed which is used for mutagenesis.

Random modification is performed by methods well-established and well-known in the art. A "randomly modified nucleotide or amino acid sequence" is a nucleotide or amino acid sequence which in a number of positions has been subjected to insertion, deletion or substitution by nucleotides or amino acids, the nature of which cannot be predicted. In many cases the random nucleotides (amino acids) or nucleotide (amino acid) sequences inserted will be "completely random" (e.g. as a consequence of randomized synthesis or PCR-mediated mutagenesis). However, the random sequences can also include sequences which have a common functional feature (e.g. reactivity with a ligand of the expression product) or the random sequences can be random in the sense that the ultimate expression product is of completely random sequence with e.g. an even distribution of the different amino acids.

In order to introduce the randomized fragments properly into the vectors, it is according to the invention preferred that the random nucleotides are introduced into the expression vector by the principle of site directed PCR-mediated mutagenesis. However, other options are known to the skilled person, and it is e.g. possible to insert synthetic random sequence libraries into the vectors as well.

To generate mutants or libraries by fusion PCR, for example three PCR reactions may carried out. Two PCR reactions are performed to generate partially overlapping intermediate fragments. A third PCR reaction is carried out to fuse the intermediate fragments.

The method for construction the library or mutant variants may include constructing a first set of primers around a desired restriction site (restriction site primer), a forward and reverse restriction primer and a second set of primers around, e.g., upstream and downstream of the codon of interest (the mutagenic primers), a forward and reverse mutagenic primer. In one embodiment, the primers are constructed immediately upstream and downstream respectively of the codon of interest. The restriction and mutagenic primers are used to construct the first intermediate and second intermediate fragments. Two PCR reactions produce these linear intermediate fragments. Each of these linear intermediate fragments comprises at least one mutated codon of interest, a flanking nucleotide sequence and a digestion site. The third PCR reaction uses the two intermediate fragments and the forward and reverse restriction primers to produce a fused linear product. The opposite, hereto for unattached ends of the linear product are digested with a restriction enzyme to create cohesive ends on the linear product. The cohesive ends of the linear product are fused by use of a DNA ligase to produce a circular product, e.g. a circular polynucleotide sequence.

To construct the intermediate fragments, the design and synthesis of two sets of forward and reverse primers are performed, a first set containing a restriction enzymes digestion site together with its flanking nucleotide sequence, and the second set contains at least one variant codon of interest (mutagenic primers). Those skilled in the art will recognize that the number of variants will depend upon the number of variant amino acid modifications desired. It is contemplated by the inventor that if other restriction enzymes are used in the process, the exact location of this digestion site and the corresponding sequence of the forward and reverse primers may be altered accordingly. Other methods are available in the art and may be used instead.

Apart from having the randomized fragment of the expression product introduced into a scaffold in accordance with the present invention, it is often necessary to couple the random sequence to a fusion partner by having the randomized nucleotide sequence fused to a nucleotide sequence encoding at least one fusion partner. Such a fusion partner can e.g. facilitate expression and/or purification/isolation and/or further stabilization of the expression product.

Random substitution or insertion of amino acids according to one example of the present invention of amino acids selected from regions 2-8 and 62-68, preferably from positions 2, 4, 6, 8, 62, 63, 64, 65, 66 and/or 68 of monomeric ubiquitin can be performed particularly easily by means of PCR since the positions mentioned are localized close to the amino or the carboxy terminus of the protein. Accordingly, the codons to be manipulated are at the 5' and 3' end of the corresponding cDNA strand. Thus, the first oligodeoxynucleotide used for a mutagenic PCR reaction apart from the codons at positions 2, 4, 6 and/or 8 to be mutated—corresponds in sequence to the coding strand for the amino terminus of ubiquitin. Accordingly, the second oligodeoxynucleotide—apart from the codons of positions 62, 63, 64, 65, 66, and/or 68 to be mutated—at least partially corresponds to the non-coding strand of the polypeptide sequence of the carboxy terminus. By means of both oligodeoxynucleotides a polymerase chain reaction can be performed using the DNA sequence encoding the monomeric ubiquitin as a template.

Furthermore, the amplification product obtained can be added to another polymerase chain reaction using flanking oligodeoxynucleotides which introduce for example recognition sequences for restriction endonucleases. It is preferred according to the invention to introduce the gene cassette obtained into a vector system suitable for use in the subsequent selection procedure for the isolation of ubiquitin variations having binding properties to a predetermined target.

Regions to be Modified in Ubiquitin

The regions for modification can be basically selected as to whether they can be accessible for said non-natural target protein of human ubiquitin, e.g. VEGF, in particular VEGF-A or its isoforms, as binding partner and whether the overall structure of the protein will presumably show tolerance to a modification.

Particularly preferred is a substitution of one or more of the surface-exposed amino acids of regions 2-8 and 62-68 of a ubiquitin monomer. Preferred are substitutions selected from amino acids of the following positions of a ubiquitin monomer, preferably mammalian (human) ubiquitin: 2, 4, 6, 8, 62, 63, 64, 65, 66, 68 of SEQ ID NO: 1 or of those amino acids corresponding to these positions. Optionally 5, 6, 7, 8, 9 of said amino acid residues are modified per monomer, in combination with adding further amino acid residues, such as an insertion of for example 2 to 15 amino acids, preferably 5 to 10 amino acids, preferably 8 amino acids, preferably in the N-terminal monomeric ubiquitin and in close proximity to said substituted amino acids. The advantage of an insertion of 2 to 15 amino acids, preferably 5 to 10 amino acids, preferably 8 amino acids in close proximity to said substituted amino acids is the extension of the binding side for the non-natural target by forming an extended, optionally a loop, structure.

After having made the modifications above, the inventors have found modified dimeric ubiquitin sequences described in the examples bind a non-natural protein target, here VEGF-A, with very high affinity and specificity.

Modified Ubiquitin Dimers Having Additional Inserts

The dimer of ubiquitin according to the invention binding to a non-natural protein target with $Kd=10^{-7}\text{-}10^{-12}M$ and exhibiting a binding activity with respect to the target shows:

(1) in the first monomeric unit substitutions of 5, 6, 7, 8, or 9 amino acids corresponding to and selected from positions 2, 4, 6, 8, 62, 63, 64, 65, 66, 68;

(2) in the second monomeric unit substitutions of 5, 6, 7, 8, or 9 corresponding to and selected from amino acid positions 2, 4, 6, 8, 62, 63, 64, 65, 66, 68; and (3) additionally an insertion of 2 to 15 amino acids in at least one monomeric ubiquitin unit in close proximity to the said substitutions.

In an embodiment, the fusion protein is a genetically fused hetero-dimer of said ubiquitin monomer having substitutions in positions 2, 4, 6, 8, 62-66, 68 of the first ubiquitin monomer and 2-15 amino acids inserted, for example between the following amino acid residues corresponding to wild-type human ubiquitin 61-62, 62-63, 63-64 and/or 64-65, and substitutions in amino acid residues in positions 2, 4, 6, 8, 62-66, 68 of the second ubiquitin monomer, preferably those shown in FIG. 1.

Preferred are the modifications in the dimeric ubiquitin to generate binding proteins for a ligand:

(1) Substitutions in the first monomeric unit at least in positions 6, 8, 62, 63, 64, 65, 66;

(2) Insertion of 8 amino acids in the first monomer;

(3) in the second monomeric unit at least in positions 6, 8, 62, 63, 64, 65, 66. Preferred are insertions of up to 8 amino acids in the c-terminal region of the monomeric ubiquitin. More preferred are insertions in those positions that are closely adjacent to the fourth beta sheet (before amino acid position 65). Most preferred are insertions in close proximity to said substitutions, preferably between amino acids 61 and 62, 62 and 63, 63 and 64, 64 and 65, most preferred between amino acids 61 and 62.

Most preferred are the following modifications to generate binding proteins for a ligand, for example to VEGF-A (variant 40401) (SEQ ID NO: 2) (see FIG. 1a)

(4) Substitutions in the first monomeric unit at least K6Y, L8D, Q62S, K63W, E64M, S65P, and T66A;

(5) Insertion of 8 amino acids of the amino acid residues DVAEYLGI in the first monomer between amino acids 61 and 62;

(6) in the second monomeric unit at least K6A, L8D, Q62R, K63D, E64T, S65V, and T66S Further variants having substitutions and insertions are shown in Table 1 and FIG. 1:

Table 1 shows preferred amino acid substitutions in hetero-dimeric ubiquitin-based VEGF-A binding proteins with 8 amino acid insertion in the first monomer (insertion not shown in this table). In dark grey (positions 6, 8, 62, 63, 64, 65, 66): substitutions in the N-terminal (first) ubiquitin monomer, in light grey (positions 6', 8', 62', 63', 64', 65', 66'): substitutions in the C-terminal (second) ubiquitin monomer of the binding protein. Further substitutions in other positions are not shown but are possible. In addition, substitutions that are not relating to the binding to a non-natural target such as substitutions in position 45, 75, and 76 are not shown. The "-" indicates that there is no substitution in this position; rather the wild-type amino acid remains. Please refer to FIG. 1 a-i for the complete sequence information.

TABLE 1

| Preferred substitutions of modified ubiquitin proteins required for binding | | | | | | | | | | | | | | | |
|---|---|---|---|---|---|---|---|---|---|---|---|---|---|---|---|
| clone ID | insert | 6 | 8 | 62 | 63 | 64 | 65 | 66 | 6' | 8' | 62' | 63' | 64' | 65' | 66' |
| 40401 | yes | Y | D | S | W | M | P | A | A | D | R | D | T | V | S |
| 59517 | yes | Y | D | S | W | M | P | A | L | S | T | R | N | Y | H |
| 59649 | yes | Y | D | S | W | M | P | A | L | R | T | S | K | — | S |
| 60423 | yes | Y | D | S | W | M | P | A | R | R | — | N | Q | F | Q |
| 60323 | yes | Y | D | S | W | M | P | A | D | E | E | Q | L | N | W |
| 60397 | yes | Y | D | S | W | M | P | A | A | D | N | D | — | — | A |
| 59507 | yes | Y | D | S | W | M | P | A | S | F | I | D | W | — | Q |
| 59987 | yes | Y | D | S | W | M | P | A | S | R | R | — | H | Y | — |
| 59603 | yes | Y | D | S | W | M | P | A | Y | A | S | E | K | K | K |

As consensus sequence for these VEGF-A binding variants (as shown in Table 1 and FIG. 1), the following consensus sequence is observed (larger letter show a high degree of identity for 9 variants) (Table 2)

TABLE 2

| One possible consensus sequence for VEGF-A binding proteins based on modified ubiquitins | | | | | | | | | | | | | |
|---|---|---|---|---|---|---|---|---|---|---|---|---|---|
| Y | D | S | W | M | P | A | A | R | R | D | K | S | S |
| | | | | | | | L | D | T | | | Y | Q |
| | | | | | | | S | | | | | | |

These alternative substitutions as shown above in each monomer can be combined with each other without any limitations provided that the resulting modified ubiquitin hetero-dimers show a specific binding affinity to VEGF-A of Kd=$10^{-7}$-$10^{-12}$M and exhibit a binding activity with respect to VEGF-A and provided that the structural stability of the ubiquitin protein is not destroyed or hampered. The binding affinities for the proteins of the invention are shown in Table 3. Shown are affinity data for the VEGF-A isoforms 121 and 165. Data have been obtained from ELISA and Biacore assays. Further data were obtained by cell proliferation assays. All assays are further described in the Examples section.

TABLE 3

| Binding Data of the preferred VEGF-A binding proteins of the invention having an insertion of 8 amino acids in the first monomer closely adjacent to the substituted amino acids (n.d. = not determined). | | | | | | |
|---|---|---|---|---|---|---|
| clone ID | insert | Affinity ELISA hVEGF121 [nM] | Affinity ELISA hVEGF165 [nM] | Affinity Biacore hVEGF121 [nM] | Affinity Biacore hVEGF165 [nM] | Cell proliferation Assay IC50 [nM] |
| 40401 | Yes | 2.5 | 2.2 | 15 | 22 | 8 |
| 59517 | Yes | 2.9 | n.d. | n.d. | n.d. | n.d. |
| 59649 | Yes | 2.8 | n.d. | 17 | 9.2 | 6.6 |
| 60423 | Yes | 3.8 | n.d. | 14 | 8 | 8 |
| 60323 | Yes | 2.3 | n.d. | 16 | 14 | 10 |
| 60397 | Yes | 2.6 | n.d. | 15 | 14 | 7.7 |
| 59507 | Yes | 4.4 | n.d. | 33 | 28 | 27 |
| 59987 | Yes | 2.5 | n.d. | 9 | 7 | 11 |
| 59603 | Yes | 21 | n.d. | n.d. | n.d. | n.d. |

Thus, in the first (N-terminal) monomer, consensus substitutions are the following: K6Y, L8D, Q62S, K63W, E64M, S65P, T66A. The insertion is located within the first monomer, closely adjacent to the $4^{th}$ (C-terminal) beta sheet and thus closely adjacent the substituted amino acids in positions 62-66 (in direction of the N-terminus), preferably between amino acids 61 and 62, 62 and 63, 63 and 64, 64 and 65, most preferred between amino acids 61 and 62. The second monomer unit for the dimeric ubiquitin shows variable substitutions, wherein in these embodiments 5-7 amino acids are substituted in positions 6, 8, 62, 63, 64, 65, and/or 66 of SEQ ID NO: 1.

Variants having substitutions and insertions to generate proteins with novel binding affinities to given targets are shown in FIG. 1 and in Table 1, Table 2 and Table 3.

In a further aspect of the invention, the present invention covers also polynucleotides which encode for a protein or a modified ubiquitin fusion protein or conjugate as described further below. Additionally, vectors comprising said polynucleotides are covered by the invention.

In an additional aspect of the present invention, host cells are covered which comprise a dimeric modified ubiquitin protein or a fusion protein or conjugate described herein and/or a polynucleotide coding for said recombinant protein or fusion protein or conjugate of the invention or a vector containing said polynucleotide.

Binding Specificities (Dissociation Constants)

The binding specificities of the proteins according to the invention are as defined above for the non-modified protein given in Kd. In accordance with the invention, the term "Kd" defines the specific binding affinity which is in accordance with the invention in the range of $10^{-7}$-$10^{-12}$ M. A value of $10^{-5}$ M and below can be considered as a quantifiable binding affinity. Depending on the application a value of $10^{-7}$ M to $10^{-11}$ M is preferred for e.g. chromatographic applications or $10^{-9}$ to $10^{-12}$ M for e.g. diagnostic or therapeutic applications. Further preferred binding affinities are in the range of $10^{-7}$ to $10^{-10}$ M, preferably to $10^{-11}$ M.

The methods for determining the binding affinities are known per se and can be selected for instance from the following methods: ELISA, Surface Plasmon Resonance (SPR) based technology (offered for instance by Biacore®), fluorescence spectroscopy, isothermal titration calorimetry (ITC), analytical ultracentrifugation, FACS.

After having made the modifications above, the inventors have found the amino acid modified ubiquitin sequences described in the examples which bind their targets with high affinity (Kd values up to $10^{-10}$ M).

Fusion Proteins and Protein Conjugates

In another preferred embodiment, the invention relates to a fusion protein or conjugate comprising a binding protein of the invention fused with of conjugated to a therapeutically (pharmaceutically) or diagnostically active component.

In a still further aspect, the invention relates to a fusion protein or conjugate comprising a hetero-dimeric binding protein of the invention fused with or conjugated to a diagnostically or therapeutically (pharmaceutically) active component. A fusion protein or conjugate of the invention may comprise non-polypeptide components, e.g. non-peptidic linkers, non-peptidic ligands, e.g. for therapeutically or diagnostically relevant radionuclides. It may also comprise small organic or non-amino acid based compounds, e.g. a sugar, oligo- or polysaccharide, fatty acid, etc. In one preferred embodiment of the invention, the hetero-ubiquitin-based binding molecule is covalently or non-covalently fused with or conjugated to a protein or peptide or chemical compound having therapeutically or diagnostically relevant properties.

One embodiment of the invention covers a fusion protein or a conjugate comprising a dimeric modified ubiquitin protein fused with or conjugated to a pharmaceutically or diagnostically active component, wherein said pharmaceutically active component is optionally a cytokine, a chemokine, a cytotoxic compound, an ubiquitin-based binding protein or an enzyme, or wherein said diagnostically active component is selected from a fluorescent compound, a photosensitizer, or a radionuclide.

The term "conjugate" as is used herein describes a multimeric modified ubiquitin which is attached either by covalent bonds or by inter-molecular interactions to a therapeutically or diagnostically molecule, e.g. a protein or a non-protein chemical substance by chemical or other suitable methods. The conjugate molecule can be attached e.g. at one or several sites through a peptide linker sequence or a carrier molecule.

The term "fusion protein" relates to a fusion protein comprising a binding or non-binding protein of the invention fused to a functional or an effector component. In one embodiment, the invention relates to a fusion protein comprising a hetero-dimeric binding protein of the invention as targeting moiety fused to a functional or an effector domain. A fusion protein of the invention may further comprise non-polypeptide components, e.g. non-peptidic linkers, non-peptidic ligands, e.g. for therapeutically or diagnostically relevant radionuclides. It may also comprise small organic or non-amino acid based compounds, e.g. a sugar, oligo- or polysaccharide, fatty acid, etc. Methods for covalently and non-covalently attaching a protein of interest to a support are well known in the art, and are thus not described in further detail here.

The term "fusion" as is used herein describes a multimeric modified ubiquitin which is fused either by covalent bonds or by molecular interactions with a therapeutically or diagnostically molecule, e.g. a protein or a non-protein chemical substance. Fusion with other protein or peptide molecules preferably takes place by genetic means. However, there is no sharp border line limiting the term "fusion" and "conjugate" so that both may overlap; for these reasons, both terms are used interchangeably.

The following gives some examples on how to obtain ubiquitin-based fusion proteins or conjugates with binding capacity to a given target, e.g. VEGF-A or its isoforms:
a) conjugation of the protein via Lysine residues present in ubiquitin;
b) conjugation of the heterodimeric ubiquitin-based binding protein via Cysteine residues—can be located C-terminal, or at any other position (e.g. amino acid residue 24 or 57); conjugation with maleimid selectable components;
c) peptidic or proteinogenic conjugations—genetic fusions (preferred C- or N-terminal);
d) "Tag"-based fusions—A protein or a peptide located either at the C- or N-terminus of the target protein. Fusion "tags", e.g. poly-histidine (particularly relevant for radiolabeling).

These and other methods for covalently and non-covalently attaching a protein of interest to a support are well known in the art, and are thus not described in further detail here.

In a further embodiment of the invention the hetero-dimeric ubiquitin-based binding protein according to the invention may contain artificial amino acids.

In further embodiments of the fusion protein or conjugate of the present invention said active component is preferably a component selected from the groups of a radionuclide either from the group of gamma-emitting isotopes, preferably $99_{Tc}$, $123_I$, $111_{In}$, or from the group of positron emitters, preferably $18_F$, $64_{Cu}$, $68_{Ga}$, $86_Y$, $124_I$, or from the group of beta-emitter, preferably $131_I$, $90_Y$, $177_{Lu}$, $67_{Cu}$, or from the group of alpha-emitter, preferably $213_{Bi}$, $211_{At}$; or a fluorescent dye, preferably Alexa Fluor or Cy dyes (Berlier et al., J. Histochem. Cytochem. 51 (12): 1699-1712, 2003); or a photosensitizer.

A further embodiment relates to fusion proteins according to the invention, further comprising a component modulating serum half-life, preferably a component selected from the group consisting of polyethylene glycol, albumin-binding peptides, and immunoglobulin or immunoglobulin fragments.

Uses of the Proteins of the Invention Binding Specifically to a Target

The modified ubiquitin binding proteins of the invention are to be used for instance for preparing diagnostic means for in vitro or in vivo use as well as therapeutic means. The proteins according to the invention can be used e.g. as direct effector molecules (modulator, antagonist, agonist) or antigen-recognizing domains.

The pharmaceutical composition of the invention can be used for treatment of cancer, e.g. breast or colon cancers, or any other tumor diseases in which VEGF-A is abundant. In addition, VEGF-A binding proteins can be used for eye diseases, such as age-related macular degeneration (AMD) or diabetic macular edema (DME).

The compositions are adapted to contain a therapeutically effective dose. The quantity of the dose to be administered depends on the organism to be treated, the type of disease, the age and weight of the patient and further factors known per se.

The invention covers a pharmaceutical composition containing a dimeric modified ubiquitin protein or a modified ubiquitin fusion protein or a conjugate or a combination thereof and a pharmaceutically acceptable carrier. The invention further covers a diagnostic agent comprising a dimeric modified ubiquitin protein or a fusion protein or conjugate with a diagnostically acceptable carrier. The compositions contain a pharmaceutically or diagnostically acceptable carrier and optionally can contain further auxiliary agents and excipients known per se. These include for example but not limited to stabilizing agents, surface-active agents, salts, buffers, colouring agents etc.

The pharmaceutical composition can be in the form of a liquid preparation, a cream, a lotion for topical application, an aerosol, in the form of powders, granules, tablets, suppositories, or capsules, in the form of an emulsion or a liposomal preparation. The compositions are preferably sterile, non-pyrogenic and isotonic and contain the pharmaceutically conventional and acceptable additives known per se. Further reference is made to the regulations of the U.S. Pharmacopoeia or Remington's Pharmaceutical Sciences, Mac Publishing Company (1990).

In the field of human and veterinary medical therapy and prophylaxis pharmaceutically effective medicaments containing at least one dimeric VEGF-A binding ubiquitin protein modified in accordance with the invention can be prepared by methods known per se. Depending on the galenic preparation these compositions can be administered parentally by injection or infusion, systemically, rectally, intraperitoneally, intramuscularly, subcutaneously, transdermally or by other conventionally employed methods of application. For applications for eye disease treatments, the direct application into the eye as drops is preferred. The type of pharmaceutical preparation depends on the type of disease to be treated, the severity of the disease, the patient to be treated and other factors known to those skilled in the art of medicine.

A "pharmaceutical composition" according to the invention may be present in the form of a composition, wherein the different active ingredients and diluents and/or carriers are in admixed with each other, or may take the form of a combined preparation, where the active ingredients are present in partially or totally distinct form. An example for such a combination or combined preparation is a kit-of-parts.

In a further embodiment, the pharmaceutical composition is in the form of a kit of parts, providing separated entities for the recombinant ubiquitin protein/fusion protein of the invention and for the one or more chemotherapeutic agents.

In a still further aspect the invention discloses diagnostic compositions comprising modified ubiquitins according to the invention specifically binding e.g. tumor-associated proteins, e.g. VEGF-A or its isoforms together with diagnostically acceptable carriers. Since enhanced expression of e.g. tumor associated molecules is correlated with tumor malignancy, the modified ubiquitins with binding capacity to said tumor-specific target molecules can also be used as a diagnostic agent for non-invasive imaging in order to gain information about e.g. VEGF in patients. Furthermore, the modified ubiquitins with binding capacity to e.g. VEGF-A and its isoforms can be used for the assessment of the response of a patient to an anti-angiogenic therapy. Due to their small size and high affinity, radiolabeled proteins based on a ubiquitin scaffold are of high importance for use as an e.g. VEGF imaging diagnostic.

In a further aspect of the invention, a recombinant protein and/or a fusion protein or conjugate is covered for use in a method of medical treatment or diagnosis.

Method of Production of the Dimeric Binding Proteins of the Invention

The binding proteins according to the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

In one aspect of the present invention, a method for generating a recombinant modified ubiquitin protein with novel binding property is provided. The method comprises at least the following steps:

a) providing an ubiquitin protein;
b) providing a non-natural target protein to human ubiquitin as potential target;
c) modifying said ubiquitin protein in order to obtain a monomeric protein having an amino acid sequence identity to the amino acid sequence of SEQ ID NO: 1 of at least 75%, wherein at least 5 and at maximum 8 amino acids are modified by substitution of amino acids corresponding to and selected from positions 2, 4, 6, 8, 62, 63, 64, 65, 66, and/or 68; and wherein 2-15 amino acids, or 6-10 amino acids, or 7-9 amino acids, or 8 amino acids are inserted in at least one of said monomers, said insertions being, in at least one monomeric ubiquitin unit within or in close proximity of said amino acid substitutions, optionally 0, 1, 2, or 3 amino acids distant from said positions, preferably between amino acids 61 and 62, 62 and 63, 63 and 64, 64 and 65, most preferred between amino acids 61 and 62,
d) fusing two of said monomeric protein units which are modified differently;
e) contacting said modified—hetero-dimeric ubiquitin protein with said target protein;
f) screening for modified hetero-dimeric ubiquitin proteins which bind to said target with a specific binding affinity of $10^{-7}$-$10^{-12}$M, and optionally
g) isolating said modified hetero-dimeric ubiquitin proteins meeting the provisions of f).

In another aspect of the present invention, a method for identifying a modified ubiquitin protein is provided. The method comprises at least the following steps:

a) providing a population of differently modified hetero-dimeric ubiquitin proteins originating from monomeric ubiquitin proteins, said population comprising hetero-dimeric ubiquitin proteins comprising two differently modified ubiquitin monomers linked together in a head-to-tail arrangement wherein each monomer of said multimeric protein is modified by substitutions of 5, 6, 7, or 8 amino acids corresponding to and selected from positions 2, 4, 6, 8, 62, 63, 64, 65, 66 and 68 of SEQ ID NO: 1, and wherein further 2-15 amino acids are inserted in at least one monomeric ubiquitin unit within or in close proximity of said amino acid substitutions, optionally 0, 1, 2, or 3 amino acids distant from said substituted amino acids corresponding to and selected from positions 2, 4, 6, 8, 62, 63, 64, 65, 66, and 68 of SEQ ID NO:1, preferably between amino acids 61 and 62, 62 and 63, 63 and 64, 64 and 65, most preferred between amino acids 61 and 62;

b) providing a non-natural ligand protein of ubiquitin as potential target;
c) contacting said hetero-dimeric modified ubiquitin with said target protein;
d) identifying a hetero-dimeric modified ubiquitin which binds to said target protein with a specific binding affinity of $10^{-7}$-$10^{-12}$M; optionally
e) isolating said hetero-dimeric modified ubiquitin with said binding affinity.

A further embodiment covers a method for generating a hetero-dimeric fusion protein or conjugate, comprising the following steps:
a) providing a hetero-dimeric modified ubiquitin;
b) fusing or conjugating said modified hetero-dimeric modified ubiquitin protein to a pharmaceutically and/or diagnostically active component.

A further embodiment covers a method of preparation of a protein as defined in the first aspect, said method comprising the following steps:
(a) preparing a nucleic acid encoding a protein as defined in the first aspect;
(b) introducing said nucleic acid into an expression vector;
(c) introducing said expression vector into a host cell;
(d) cultivating the host cell;
(e) subjecting the host cell to culturing conditions under which a fusion protein is expressed from said vector, thereby producing a protein as defined in the first aspect;
(f) optionally isolating the protein produced in step (e).

In one embodiment, the protein produced in step (e) is in the form of inclusion bodies. In a further preferred embodiment, the method further comprises the steps: isolating the inclusion bodies; solubilizing said inclusion bodies, thereby obtaining soluble fusion proteins; and further purifying the soluble fusion proteins obtained in the preceding step by at least two chromatographic steps. Suitable chromatographic steps include without limitation size-exclusion chromatography, anion exchange chromatography and cation exchange chromatography.

Optionally, the modification may be performed by genetic engineering on the DNA level and expression of the modified protein in prokaryotic or eukaryotic organisms or in vitro. In a further embodiment, said modification step includes a chemical synthesis step. In one aspect of the invention, said population of differently modified proteins is obtained by genetically fusing two DNA libraries encoding each for differently modified monomeric ubiquitin proteins. In a still further aspect, said method is adapted in order that said modified dimeric ubiquitin protein is fused with a diagnostic component, or wherein said recombinant modified dimeric ubiquitin protein is formed via said diagnostic component. According to the invention, a modified protein can further be prepared by chemical synthesis. In this embodiment the steps c) to d) of claim 1 are then performed in one step.

In a further aspect, the present invention is directed to a library containing DNA encoding for modified monomeric ubiquitin proteins as defined above which form the basis for providing the hetero-dimeric ubiquitin proteins of the invention. In a still further aspect of the invention, a fusion library containing DNA obtained by fusing two libraries as specified above is provided each library encoding for identically or differently modified ubiquitin monomers in order to obtain homo- or hetero-dimeric ubiquitin fusion proteins, the monomers thereof being linked together in a head-to-tail arrangement, said library encoding for homo- or hetero-dimeric fusion proteins of ubiquitin exhibiting a binding activity with respect to a ligand. Said linking together is performed either by using anyone of the linkers known by the skilled artisan or a linker described herein.

Example 1 outlines the production of a complex library. However, care must be taken as regards the quality of such a library. Quality of a library in scaffold technology is in the first place dependent from its complexity (number of individual variants) as well as functionality (structural and protein-chemical integrity of the resulting candidates). Both characteristics, however, may exert negative influences on each other: enhancing the complexity of a library by increasing the number of modified positions on the scaffold might lead to a deterioration of the protein-chemical characteristics of the variants. This might result in a decreased solubility, aggregation and/or low yields. A reason for this is the larger deviation from native scaffolds having an energetically favourable protein packaging. Therefore, it is a balancing act to construct such a scaffold library suitably between the extreme positions of introducing as many variations as possible into the original sequence in order to optimize it for a target and, on the other hand, of conserving the original primary sequence as much as possible in order to avoid negative protein-chemical effects. It is noted that the present disclosure encompasses also each conceivable combination of the features described herein in view of the aspects or embodiments of the invention.

Selection of the Modified Ubiquitin Proteins with Binding Affinity and Determination of the Modified Amino Acids Responsible for the Binding Affinity After e.g. at least two different DNA libraries encoding for dimeric modified ubiquitin proteins have been established by differently modifying selected amino acids in each of the monomeric ubiquitin units (ubiquitin monomers), these libraries are genetically fused by e.g. linker technology to obtain DNA molecules encoding for hetero-dimeric modified ubiquitin proteins. The DNA of these libraries is expressed into proteins and the modified dimeric proteins obtained thereby are contacted according to the invention with the ligand VEGF-A to optionally enable binding of the partners to each other if a binding affinity does exist.

It is a crucial aspect of the invention that the contacting and screening process is performed already with respect to the homo- or hetero-dimeric ubiquitin protein. This process enables screening on those ubiquitin proteins which provide a binding activity to a given target.

Contacting according to the invention is preferably performed by means of a suitable presentation and selection method such as the phage display, ribosomal display, mRNA display or cell surface display, yeast surface display or bacterial surface display methods, preferably by means of the phage display method. For complete disclosure, reference is made also to the following references: Hoess, Curr. Opin. Struct. Biol. 3 (1993), 572-579; Wells and Lowmann, Curr. Opin. Struct. Biol. 2 (1992), 597-604; Kay et al., Phage Display of Peptides and Proteins-A Laboratory Manual (1996), Academic Press. The methods mentioned above are known to those skilled in the art and can be used according to the invention including modifications thereof.

The determination whether the modified protein has a quantifiable binding affinity with respect to a predetermined binding partner can be performed according to the invention preferably by one or more of the following methods: ELISA, plasmon surface resonance spectroscopy, fluorescence spectroscopy, FACS, isothermal titration calorimetry and analytical ultracentrifugation.

Characterization of the Dimeric Binding Proteins

The further characterization of the ubiquitin variations obtained in this manner can be performed in the form of a soluble protein as detailed above after cloning of the corresponding gene cassette into a suitable expression vector. The appropriate methods are known to those skilled in the art or described in the literature. Exemplary methods for characterization of dimeric binding proteins are outlined in the Examples section of this invention.

Preferably, the step of detection of the proteins having a binding affinity with respect to a predetermined binding partner is followed by a step of isolation and/or enrichment of the detected protein.

Following the expression of the ubiquitin protein modified according to the invention, it can be further purified and enriched by methods known per se. The selected methods depend on several factors known per se to those skilled in the art, for example the expression vector used, the host organism, the intended field of use, the size of the protein and other factors. For simplified purification the protein modified according to the invention can be fused to other peptide sequences having an increased affinity to separation materials. Preferably, such fusions are selected that do not have a detrimental effect on the functionality of the ubiquitin protein or can be separated after the purification due to the introduction of specific protease cleavage sites. Such methods are also known per se to those skilled in the art.

Vectors, Host Cells and Methods of Production of Proteins

Vectors may be expression and cloning vectors containing a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the modified ubiquitin scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the modified ubiquitin based scaffold protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 1988, 6:47).

BRIEF DESCRIPTION OF THE DRAWINGS

FIG. 1 shows different dimeric modified ubiquitin binding proteins with inserts. The linker sequence (here: GIG) is shown in italics. Not substituted amino acids of the ubiquitin monomers and of the linker are shown in blue (highlighted); substituted amino acids are not highlighted and appear with white background. In all variants shown here, in the N-terminal (first) monomer, the modifications account to at least 15 amino acids that are substituted and inserted to generate a new binding property to a non-natural protein target (about at least 20% of all amino acids of the first monomer). Further 3 amino acids (e.g. at positions 45, 75, 76) are substituted to improve biochemical properties, but not being related to the binding to a target.

FIG. 1a shows the amino acid sequence of VEGF-A binding protein 40401 (SEQ ID NO: 2). The clone is substituted in positions 6, 8, 62-66 in both ubiquitin units and shows an additional insertion of 8 amino acids in position 61-62 of the first ubiquitin monomer.

FIG. 1b shows the amino acid sequence of VEGF-A binding protein 59517 (SEQ ID NO: 3). The clone is substituted in positions 6, 8, 62-66 in both ubiquitin monomers and shows an additional insertion of 8 amino acids. Thus, within the second monomer 7 amino acids (9% of all amino acids) are modified that are involved in a novel binding property to a given protein target.

FIG. 1c shows the amino acid sequence of VEGF-A binding protein 59649 (SEQ ID NO: 4). The clone is substituted in positions 6, 8, 62-66 in the first ubiquitin unit and positions 6, 8, 62, 63, 65, and 66 of the second ubiquitin unit. The protein shows an additional insertion of 8 amino acids. Thus, within the second monomer 6 amino acids (8% of all amino acids) are modified that are involved in a novel binding property to a given protein target.

FIG. 1d shows the amino acid sequence of VEGF-A binding protein 60423 (SEQ ID NO: 5). The clone is substituted in positions 6, 8, 62-66 in the first ubiquitin unit and positions 6, 8, 63-66 of the second ubiquitin unit. The protein shows an additional insertion of 8 amino acids. Thus, within the second monomer 6 amino acids (8% of all amino acids) are modified that are involved in a novel binding property to a given protein target.

FIG. 1e shows the amino acid sequence of VEGF-A binding protein 60323 (SEQ ID NO: 6). The clone is substituted in positions 6, 8, 62-66 in both ubiquitin units and shows an additional insertion of 8 amino acids. Thus, within the second monomer 7 amino acids (9% of all amino acids) are modified that are involved in a novel binding property to a given protein target.

FIG. 1f shows the amino acid sequence of VEGF-A binding protein 60397 (SEQ ID NO: 7). The clone is substituted in positions 6, 8, 62-66 in the first ubiquitin unit and positions 6, 8, 62, 63, and 66 of the second ubiquitin unit. The protein shows an insertion of 8 amino acids. An additional exchange is found in position 51 of the second ubiquitin unit. Thus, within the second monomer 6 amino acids (8% of all amino acids) are modified that are involved in a novel binding property to a given protein target.

FIG. 1g shows the amino acid sequence of VEGF-A binding protein 59507 (SEQ ID NO: 8). The clone is substituted in positions 6, 8, 62-66 in the first ubiquitin unit and positions 6, 8, 62-64, and 66 of the second ubiquitin unit. The protein shows an insertion of 8 amino acids between positions 61 and 62. An additional exchange is found in position 47 of the first ubiquitin unit. Thus, within the second monomer 7 amino acids (9% of all amino acids) are modified that are involved in a novel binding property to a given protein target.

FIG. 1h shows the amino acid sequence of VEGF-A binding protein 59987 (SEQ ID NO: 9). The clone is substituted in positions 6, 8, 62-66 in the first ubiquitin unit and positions 6, 8, 62, 64, and 65 of the second ubiquitin unit. The protein shows an additional insertion of 8 amino acids. Thus, within the second monomer 5 amino acids (6.5% of all amino acids) are modified that are involved in a novel binding property to a given protein target.

FIG. 1i shows the amino acid sequence of VEGF-A binding protein 59603 (SEQ ID NO: 10). The clone is substituted in positions 6, 8, 62-66 in both ubiquitin units and shows an insertion of 8 amino acids. Additional exchanges are found in positions 48 of the first ubiquitin unit and position 2 of the second ubiquitin moiety. Thus, within the second monomer 9 amino acids (12% of all amino acids) are modified that are involved in a novel binding property to a given protein target.

FIG. 1j shows the amino acid sequence of dimeric ubiquitin used as basis for substitutions to generate high specific binding proteins (SEQ ID NO: 11). Positions 6, 8, 62-66 in both ubiquitin units are marked with an X. An amino acid sequence for a linker is not shown since any possible linker known in the art could be used or even no linker could be used. Note that compared to wildtype the ubiquitin is further modified in position 45 in both monomers to Tryptophan. This modification does not influence the binding. At the last C-terminal amino acid in the first monomer, there is either Glycine or an exchange from Glycine to Alanine at the last C-terminal amino acids of the first monomer. These exchanges at positions 45, 75, 76 are optional and do not influence the binding to a protein ligand/target.

FIG. 2 shows high affinity binding of binding protein 40401 (SEQ ID NO: 2) to VEGF-A. The binding is shown by closed circles connected by a fitted line. The figure shows a concentration dependent ELISA of the binding of the hetero-dimeric ubiquitin variant to human VEGF-A, in particular to isoform 121 and to isoform 165. As negative control, NGF was used (symbol—star-connected by a broken line). Variant 40401 (also referred to as SPVF-11_1211_A1_TsX6 in this figure) shows high affinity binding to VEGF-A 121 (Kd=2.5 nM=$2.5 \times 10^{-9}$ M) and to VEGF-A 165 (Kd=2.2 nM=$2.2 \times 10^{-9}$ M). The binding affinities to VEGF-A 121 and to VEGF-A 165 are very similar.

EXAMPLES

Figure 2:
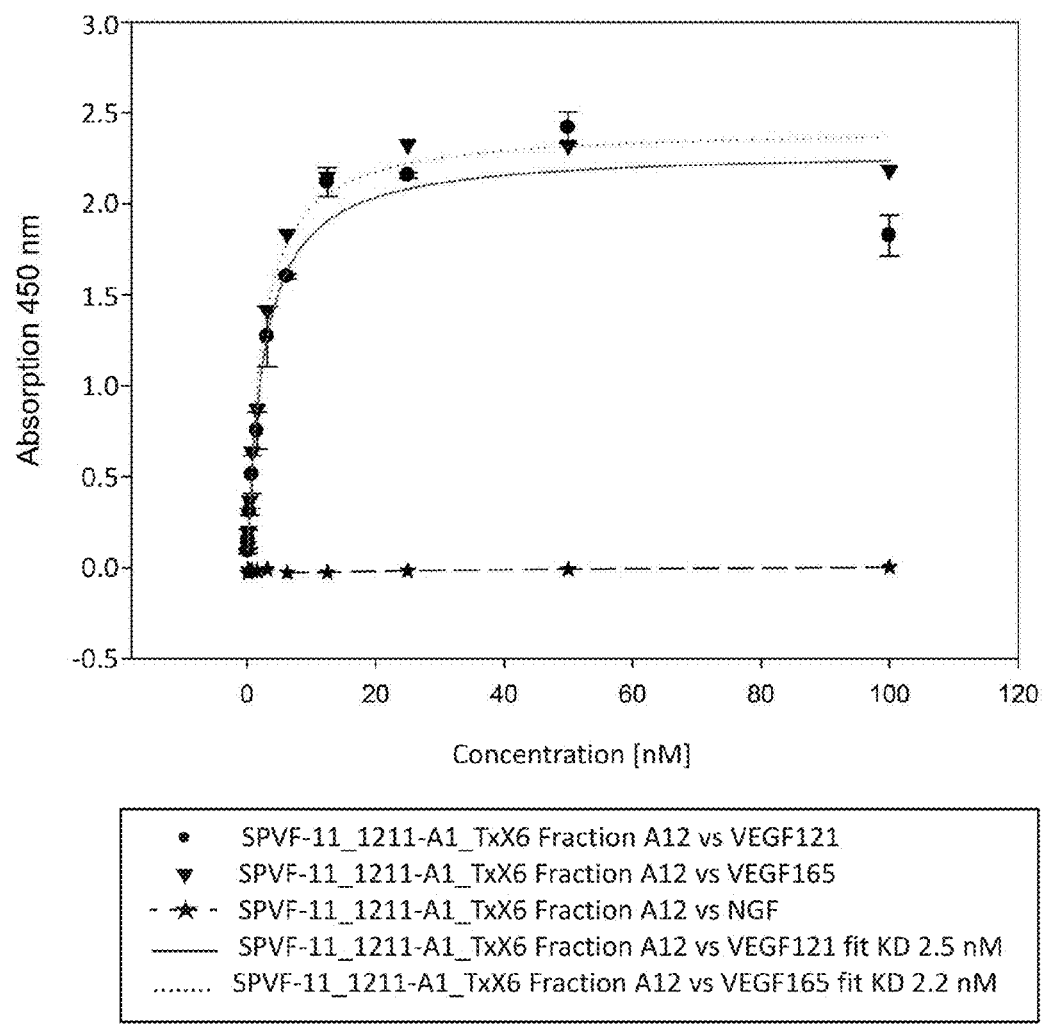

The following Examples are provided for further illustration of the invention. The invention is particularly demonstrated with respect to the modification of ubiquitin as an example. The invention, however, is not limited thereto, and the following Examples merely show the practicability of the invention on the basis of the above description. For a complete disclosure of the invention reference is made also to the literature cited in the application and in the annex which are all incorporated in their entirety into the application by reference.

Example 1

Identification of Hetero-Dimeric Binding Proteins Based on Modified Ubiquitin Proteins Having Insertions (Extended Structures)

Library Construction and Cloning

Unless otherwise indicated, established recombinant genetic methods were used, for example as described in Sambrook et al. A random library of human ubiquitin hetero-dimers with high complexity was prepared by concerted mutagenesis of at least 14 selected amino acid positions. The modified amino acids, which were substituted by NNK triplets, comprised amino acids selected from positions 6, 8, 62, 63, 64, 65, 66 within the proximal/N-terminal (first) ubiquitin monomer and amino acids selected from positions 6, 8, 62, 63, 64, 65, 66 within the distal/C-terminal (second) ubiquitin monomer. Both ubiquitin monomers were genetically linked (head to tail) by a Glycine/Serine linker with at least the sequence GIG or at least the sequence SGGGG, for example GIG, SGGGG, SGGGGIG, SGGGGSGGGGIG or SGGGGSGGGG, but any other or no linker is possible.

The Target Protein VEGF-A

VEGF-A exists in several isoforms. VEGF121 and VEGF165 are naturally abundant isoforms of VEGF-A (accession number p15692). VEGF121 (Accession Number p15692-9) and VEGF165 (accession number p15692-9) were purchased from Humanzyme (order numbers HZ-1206 (VEGF121) and HZ-1153 (VEGF165)). Compared to the data base entry, isoform VEGF165 is 26 amino acids shorter because the signal peptide is not included. Both isoforms were expressed in human cells to ensure a correct glycolysation.

TAT Phage Display Selection

The heterodimeric ubiquitin library was enriched against VEGF-A using, for example, TAT phage display as selection system. Other selection methods known in the art can be used. The target can be immobilized non-specifically onto protein binding surfaces or via biotinylated residues which were covalently coupled to the protein. The immobilization via biotin onto streptavidin beads or neutravidin strips is preferred. The target-binding phages are selected either in solution or on immobilized target; for example, the biotinylated and immobilized target with phage was incubated followed by washing of the phages bound to the matrix and by elution of matrix-bound phages. In each cycle following target incubation, the beads were magnetically separated from solution and washed several times. In the first selection cycle the biotinylated target was immobilized to neutravidin strips whereas in cycles two to four selections in solution were performed followed by immobilization of target-phage complexes on Streptavidin-coated Dynabeads® (Invitrogen). After washing in the first two selection cycles the phages of target-binding modified ubiquitin molecules were released by elution with acidic solution. In selection cycles three and four elution of phages was carried out by competitive elution with excess target. The eluted phages were reamplified. To direct specificity of binders a protein similar to the target can be included during selection.

Alternatively to TAT Phage Display Selection: Ribosome Display Selection

The ubiquitin library was enriched against the target using, for example, ribosome display as selection system. Other selection methods known in the art can be used. The target was biotinylated according to standard methods and immobilized on Streptavidin-coated Dynabeads® (Invitrogen). Ternary complexes comprising ribosomes, mRNA and nascent ubiquitin polypeptide were assembled using the PURExpress™ In Vitro Protein Synthesis Kit (NEB). Up to four primary rounds of selection were performed, wherein ternary complexes were incubated followed by two similar rounds of selection. In each cycle following target incubation, the beads were magnetically separated from solution and washed with ribosome display buffer with increasing stringency. After washing in the first two selection cycles, the beads were again magnetically separated from solution and mRNA of target-binding modified ubiquitin molecules was released from ribosomes by addition of 50 mM EDTA. In selection cycles three and four elution of mRNA complex was carried out by competitive elution with excess target (Lipovsek and Pluckthun, 2004). After each cycle, RNA purification and cDNA synthesis were performed using RNeasy MinElute Cleanup Kit (Qiagen, Germany), Turbo DNA-free Kit (Applied Biosystems, USA) and Transcriptor Reverse Transcriptase (Roche, Germany).

Cloning of Enriched Pools

After the fourth selection cycle the synthesized cDNA was amplified by PCR, cut with suitable restriction nucleases and ligated into an expression vector via compatible cohesive ends.

Single Colony Hit Analysis

After transformation into NovaBlue (DE3) cells (Merck, Germany) ampicillin-resistant single colonies were grown in SOB medium containing 100 µg/ml ampicilin and 20 g/l glucose. Expression of the VEGF-A binding modified ubiquitin was achieved by cultivation in 96-well deep well plates using auto induction medium ZYM-5052 (Studier, 2005). Cells were harvested and subsequently lysed. After centrifugation the resulting supernatants were screened by ELISA using Nunc MediSorp plates (Thermo Fisher Scientific, USA) coated with 4 µg/ml VEGF-A and a ubiquitin-specific Fab fragment conjugated with horseradish peroxidase (POD). As detecting reagent TMB-Plus (KEM-EN-Tec) was used and the yellow colour was developed using 0.2 M $H_2SO_4$ solution and measured in a plate reader at 450 nm versus 620 nm.

Usually, several, for example, four cycles of selection display versus VEGF-A were carried out. In the last two cycles of selection binding molecules were eluted with an excess of free VEGF-A. The binding molecules were further selected by maturation.

Maturation of Selected VEGF-A Binding Clones with High Affinities

In order to enhance the affinity ubiquitin-based dimeric binding proteins to VEGF-A, ubiquitin building units (monomers) of a dimer of selected binding proteins were fused to naïve monomeric ubiquitin libraries. For example, either the N-terminal or C-terminal monomer of a dimeric ubiquitin binding unit was fused to a monomeric ubiquitin library. Several, for example, 1 to 10, preferably 3, VEGF-A binding molecules were selected and the N-terminal ubiquitin monomer with substitutions in positions 6, 8, 62, 63, 64, 65, and/or 66, and optionally an insertion at position 61-62, was fused to naïve monomeric ubiquitin libraries with randomized amino acid positions 6, 8, 62, 63, 64, 65, and/or 66 via a suitable amino acid linker, for example GIG. In parallel, ubiquitin monomers of the C-terminal region of a hetero-dimeric binding protein having substitutions in positions 6, 8, 62, 63, 64, 65, and/or 66 were fused to naïve monomeric ubiquitin libraries with randomized amino acid positions 6, 8, 62, 63, 64, 65 and/or 66 and/or 42, 44, 68, 70, and 72-74 via a suitable amino acid linker, for example GIG. The resulting dimeric ubiquitin libraries with up to 7 randomized positions were pooled and exhibited a theoretical number of around $1.5 \times 10^{10}$ different variants which could be fully displayed in a ribosome display with up to 10-fold presentation of each variant using methods known to somebody skilled in the art. The mixed library was applied to 4 rounds of ribosome display including 3 rounds competitive elution of VEGF-A binding molecules with soluble VEGF121.

VEGF-A binders with high affinity to VEGF-A do not always form complexes which are stable for a longer period of time. Some complexes (ubiquitin-dimer and VEGF-A) have high off-rates, meaning that the binding is strong but the complex differentiates quickly. A lower off-rate as determined e.g. by Biacore assays is desirable. Thus, to differentiate stable VEGF-A binding complexes from variants with high affinities but high off-rates, one round with 16 hrs off-rate selection was performed. The elution is performed under competitive conditions with 1000× non bound target protein (compared to the target protein which is bound to e.g. streptavidin-beads). All binders which are still bound to the immobilized target protein after 16h are further analyzed. After this selection, pools with VEGF-A binding molecules were subcloned to an expression vector using standard methods known to a skilled person and probed for binding to different types of VEGF-A in hit-screening (e.g. ELISA) as described below.

Some exemplary VEGF-A binding proteins having inserts, for example 40401, are shown in FIG. 1 and in Tables 1, 2 and 3. The binding proteins were analysed as described in Example 2.

Example 2

Binding Analysis of Modified Ubiquitin-Based Binding Proteins to Human VEGF-A

Example 2A

Figure 3:
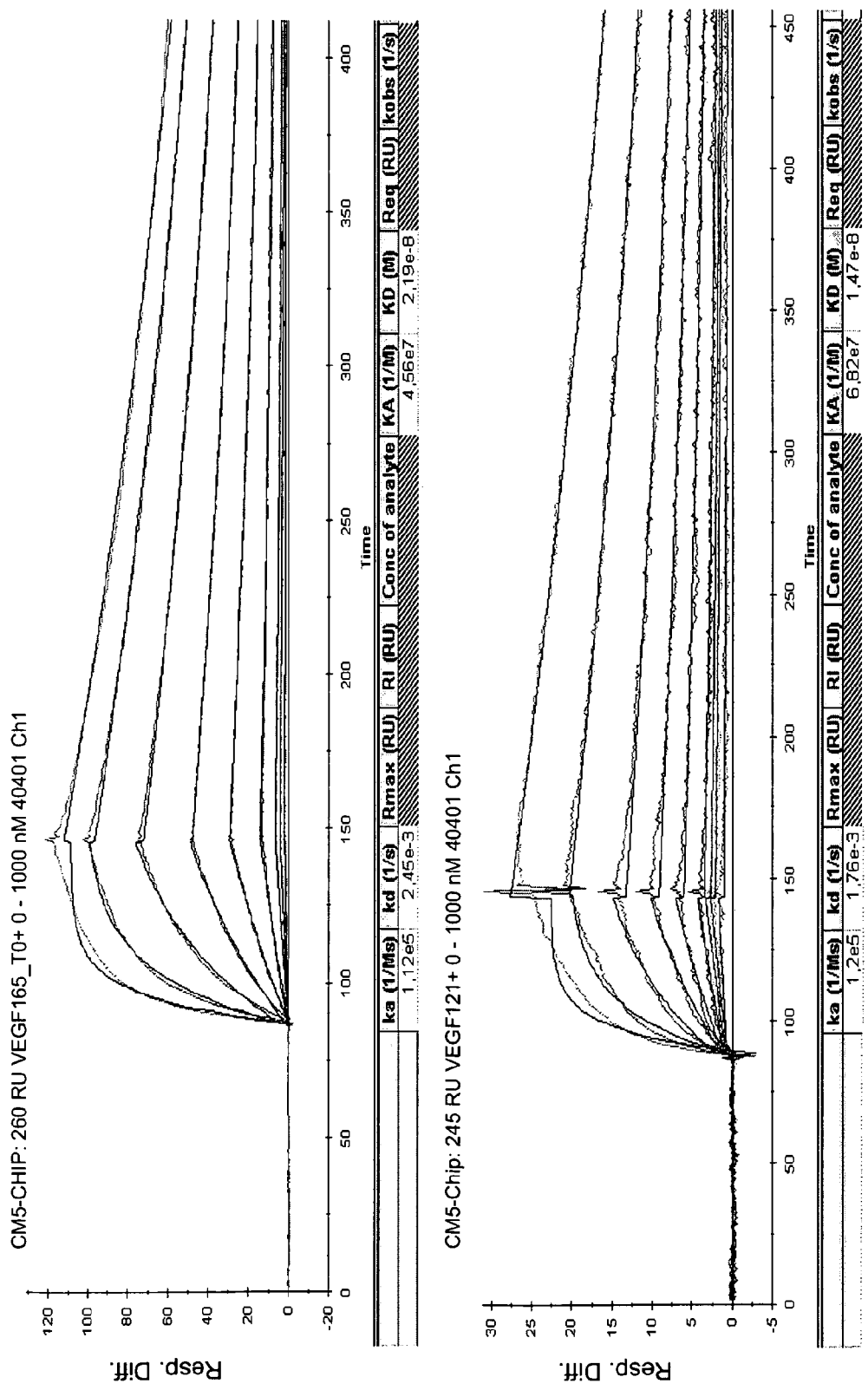
FIG. 3 shows results of an analysis of the modified hetero-dimeric ubiquitin molecule 40401 via label-free interaction assays using Surface Plasmon Resonance (Biacore®). Different concentrations of hetero-dimeric ubiquitin variants were selected (0-1000 nM) for binding to either VEGF121 or VEGF165 immobilized on a chip (Biacore) to evaluate the interaction between the hetero-dimeric variant 40401 and VEGF-A. Analyzing the association and dissociation curves resulted in a Kd of $2.2 \times 10^{-8}$ M ($k_{off}$ rate of $2.45 \times 10^{-3}$ s$^{-1}$) to VEGF165 and a Kd of $1.5 \times 10^{-8}$ M ($k_{off}$ rate of $1.76 \times 10^{-3}$ s$^{-1}$) to VEGF121 which indicates a long half time of a complex of 40401 and VEGF-A.

Binding Analysis of Modified Ubiquitin-Based VEGF Binding Variants by Concentration Dependent ELISA Binding of ubiquitin-based variants to human VEGF-A was assayed by a concentration dependent ELISA. Increasing amounts of purified protein applied to NUNC-medisorp plates coated with human VEGF-A 121 or VEGF-A 165 and NGF as negative control. Antigen coating with 1 to 2.5 μg/ml per well was performed at 4° C. overnight. After washing the plates with PBS, 0.1% Tween 20 pH 7.4 (PBST) the wells were blocked using blocking solution (PBS pH 7.4; 3% BSA; 0.5% Tween 20) at room temperature for 2 h. Wells were washed again three times with PBST. Different concentrations of modified ubiquitin based VEGF-A binding protein were then incubated in the wells at RT for 1 h (see FIG. 3). After washing the wells with PBST, the anti-Ubi fab fragment (a-Ubi-Fab) POD conjugate was applied in an appropriate dilution (for example, 1:6500) in PBST. The plate was washed three times with 300 μl buffer PBST/well. 50 μl TMB substrate solution (KEM-EN-Tec) were added to each well and was incubated. The reaction was stopped by adding 0.2 M $H_2SO_4$ per well. The ELISA plates were read out using the TECAN Sunrise ELISA-Reader. The photometric absorbance measurements were done at 450 nm using 620 nm as a reference wavelength. FIG. 3a shows clearly the very high affinity binding of 40401 (SEQ ID NO: 2) to VEGF-A with an apparent KD value of 2.2 to 2.5 nM. Further examples are shown in FIG. 3. Thus, only very few modifications (up to 6 substitutions in each monomer) in the ubiquitin-wildtype result in a high affinity binding to VEGF-A. FIG. 2 shows clearly the very high affinity binding of 40401 (SEQ ID NO: 2) to VEGF-A with an apparent KD value of 2.2 to 2.5 nM. No variant showed binding to the control (NGF). Further results of other VEGF-A binding proteins are shown in Table 2 (above).

Example 2B

Figure 4:
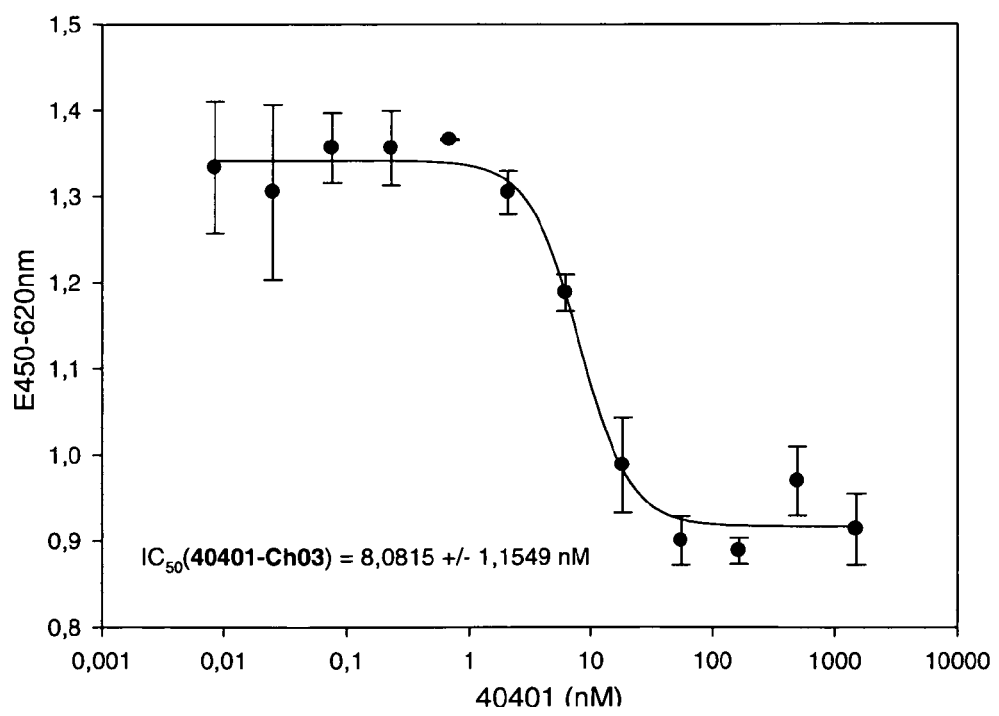
FIG. 4 shows inhibition of VEGF-A-induced proliferation of HUVEC by the binding protein 40401. Different concentrations of 40401 were preincubated with VEGF-A in medium together with a fixed VEGF-A concentration and the mixture applied to growing HUVEC. After three days the proliferation of cells was quantified with WST reagent. The dose response curve was fitted and an IC50 of 8 nM was calculated.

Binding Analysis of Modified Ubiquitin-Based VEGF Binding Variants by Biacore Assays Different concentrations of the variant were analyzed (for example, 0-450 nM of the variant, preferably 40401) for binding to VEGF immobilized on a CM5-chip (Biacore®) using methods known to those skilled in the art. The obtained data were processed via the BIAevaluation software and 1:1-Langmuir-fitting. The $K_D$ of 40401 for VEGF165 was $2.2 \times 10^{-8}$ M, as shown in FIG. 4. The kinetic binding constants are shown in FIG. 4 and in Table 2. Further results of other VEGF-A binding proteins are shown in Table 2 (above).

Example 3

Inhibition of VEGF Stimulated Cell Proliferation by Modified Hetero-Dimeric Ubiquitin Based Binding Proteins of the Invention Inhibition of VEGF stimulated HUVEC cell proliferation was assessed with the following assay: HUVEC cells (Promocell) were grown in Hams F-12 Nutrient Mixture (Kaighn's Modification, Gibco) with 10% FCS, 0.1 mg/ml Heparin, 10 ng/ml b-FGF and passages 5 and 6 were used. On day one, 6000 cells were seeded in complete medium in collagen coated 96 well plates. On the following day, cells were preincubated with 100% Hams F12 Nutrient Mixture for 6 h. After this time, the medium was exchanged for the preincubation mix, prepared of medium containing 5% FCS, 0.1 mg/ml Heparin and gentamycin supplemented with dilution series of the VEGF-specific binding protein premixed with 15 ng/ml VEGF121 (Biomol/Humanzyme). The dilution series were prepared in 1:3 steps (starting from 1.5 μM as indicated and incubated 1 h at room temperature. Each concentration was run in triplicate. VEGF-specific therapeutic monoclonal antibody Avastin® (Roche) was used as control (not shown). Viability of the cells was assessed after 3 days with WST reagent (Roche) according to the manufacturer's instructions. Results of this inhibition assay are shown in FIG. 4 and Table 2. Further results of other VEGF-A binding proteins are shown in Table 2 (above). The binding protein of the invention clearly shows a significant inhibition of VEGF-A induced proliferation of HUVEC cells.

The invention claimed is:

1. A hetero-dimeric modified ubiquitin protein with binding capability to a non-natural target protein of human ubiquitin, comprising
two ubiquitin monomers linked together in a head-to-tail arrangement,
wherein both monomers of said hetero-dimeric protein are differently modified at least by substitutions of at least 5, 6, 7, or 8 amino acids corresponding to positions 2, 4, 6, 8, 62, 63, 64, 65, 66, and 68 of SEQ ID NO: 1, and
wherein 2-15 amino acids are inserted in at least one ubiquitin monomer 0, 1, 2, or 3 amino acids distant from said amino acid substitutions corresponding to positions 2, 4, 6, 8, 62, 63, 64, 65, 66, and 68 of SEQ ID NO:1, and
wherein said modified ubiquitin monomers have an amino acid identity to SEQ ID NO: 1 of at least 75% and said modified hetero-dimeric ubiquitin have a specific detectable binding affinity to said non-natural target protein of Kd=$10^{-7}$-$10^{-12}$ M.

2. A hetero-dimeric modified ubiquitin protein of claim 1, wherein 6 to 10 amino acids or 7 to 9 amino acids or 8 amino acids are inserted in one or both ubiquitin monomers.

3. A hetero-dimeric modified ubiquitin protein according to claim 1, wherein the insertion of amino acids is 0, 1, 2, 3, 4, or 5 amino acids distant from the C-terminal (fourth) or the N-terminal (first) beta strand, optionally wherein said insertion is located in the N-terminal (first) ubiquitin monomer.

4. A hetero-dimeric modified ubiquitin protein according to claim 2 wherein the insertion is between amino acids corresponding to amino acid positions 61 and 62 or positions 62 and 63 or positions 63 and 64 or positions 64 and 65 of SEQ ID NO: 1, most preferred between amino acids corresponding to positions 61 and 62 of SEQ ID NO: 1.

5. A hetero-dimeric modified ubiquitin protein according to claim 1, wherein the non-natural target protein is vascular endothelial growth factor (VEGF), preferably VEGF-A or its isoforms.

6. A hetero-dimeric modified ubiquitin protein with binding capability to a vascular endothelial growth factor (VEGF) protein, the hetero-dimeric modified ubiquitin protein comprising two ubiquitin monomers linked together in a head-to-tail arrangement, wherein:
(i) both monomers of said hetero-dimeric protein are differently modified at least by substitutions of at least 5, 6, 7, or 8 amino acids corresponding to positions 2, 4, 6, 8, 62, 63, 64, 65, 66, and 68 of SEQ ID NO: 1; and
(ii) 2-15 amino acids are inserted in at least one ubiquitin monomer 0, 1, 2, or 3 amino acids distant from said amino acid substitutions corresponding to positions 2, 4, 6, 8, 62, 63, 64, 65, 66, and 68 of SEQ ID NO: 1, and
(iii) said modified ubiquitin monomers have an amino acid identity to SEQ ID NO: 1 of at least 75% and said modified hetero-dimeric ubiquitin have a specific detectable binding affinity to said VEGF of Kd =$10^{-7}$-$10^{-12}$M, and further wherein substitutions in the N-terminal (first) monomer are K6Y, L8D, Q62S, K63W, E64M, S65P, T66A, and/or wherein the insertion within the N-terminal monomer comprises or consists of the amino acid sequence DVAEYLGI (SEQ ID NO: 12).

7. A fusion protein or a conjugate comprising a hetero-dimeric modified ubiquitin protein according to claim 1 fused with or conjugated to a pharmaceutically active component or to a diagnostically active component selected from the group consisting of a fluorescent compound, a photosensitizer, and a radionuclide.

8. A multimer of a hetero-dimeric modified ubiquitin protein according to claim 1.

9. A pharmaceutical composition containing a hetero-dimeric modified ubiquitin protein according to claim 1 and a pharmaceutically acceptable carrier or a diagnostically acceptable carrier.

10. A diagnostic agent comprising a hetero-dimeric modified ubiquitin protein according to claim 1 with a diagnostically acceptable carrier.

11. A polynucleotide coding for a hetero-dimeric modified ubiquitin protein according to claim 1.

12. A vector comprising a polynucleotide according to claim 11.

13. A host cell comprising a hetero-dimeric modified ubiquitin protein according to claim 1.

14. A method for generating a hetero-dimeric modified ubiquitin protein according to claim 1, the method comprising:
a) providing an ubiquitin protein;
b) providing a non-natural target protein of ubiquitin as potential target;
c) modifying said ubiquitin protein in order to obtain a monomeric ubiquitin protein having an amino acid sequence identity to the amino acid sequence of SEQ ID NO: 1 of at least 75%, wherein 5, 6, 7, or 8 amino acids are modified at least by substitution of amino acids corresponding to positions 2, 4, 6, 8, 62, 63, 64, 65, 66, and/or 68 of SEQ ID NO: 1, and wherein further 2-15 amino acids are inserted 0, 1, 2, or 3 amino acids distant from said substituted amino acids corresponding to positions 2, 4, 6, 8, 62, 63, 64, 65, 66, and 68 of SEQ ID NO:1
d) linking two of said monomeric differently modified ubiquitin monomers;
e) contacting said hetero-dimeric modified ubiquitin protein with said target protein;
f) identifying modified hetero-dimeric modified ubiquitin proteins which bind to said target protein with a specific binding affinity of $10^{-7}$-$10^{-12}$ M, and optionally
g) isolating said hetero-dimeric modified ubiquitin proteins.

15. A method for identifying a hetero-dimeric modified ubiquitin protein according to claim 1, the method comprising:
a) providing a population of differently modified hetero-dimeric ubiquitin proteins originating from monomeric ubiquitin proteins, said population comprising hetero-dimeric ubiquitin proteins comprising two differently modified ubiquitin monomers linked together in a head-to-tail arrangement wherein each monomer of said multimeric protein is modified by substitutions of 5, 6, 7, or 8 amino acids corresponding to positions 2, 4, 6, 8, 62, 63, 64, 65, 66 and 68 of SEQ ID NO: 1,and wherein further 2-15 amino acids are inserted in at least one monomeric ubiquitin unit within or in close proximity of said amino acid substitutions, optionally 0, 1, 2, or 3 amino acids distant from said substituted amino acids corresponding to positions 2, 4, 6, 8, 62, 63, 64, 65, 66, and 68 of SEQ ID NO:1,
b) providing a non-natural ligand protein of ubiquitin as potential target;
c) contacting said hetero-dimeric modified ubiquitin with said target protein; and
d) identifying a hetero-dimeric modified ubiquitin which binds to said target protein with a specific binding affinity of $10^{-7}$-$10^{-12}$ M; and optionally
e) isolating said hetero-dimeric modified ubiquitin with said binding affinity.

16. A method for generating a hetero-dimeric fusion protein or conjugate, the method comprising:
a) providing a dimeric modified ubiquitin according to claim 1; and
b) fusing or conjugating said modified dimeric modified ubiquitin protein to a pharmaceutically active component and/or to a diagnostically active component selected from the group consisting of a fluorescent compound, a photosensitizer, or a radionuclide.

17. The fusion protein or the conjugate of claim 7, wherein the pharmaceutically active component, if present, is selected from the group consisting of a cytokine, a chemokine, a cytotoxic compound, a ubiquitin based binding protein, and an enzyme.

18. The method of claim 16, wherein the pharmaceutically active component, if present, is selected from the group consisting of a cytokine, a chemokine, a cytotoxic compound, a ubiquitin based binding protein, and an enzyme.

19. The hetero-dimeric modified ubiquitin protein of claim 6, wherein the vascular endothelial growth factor is selected from the group consisting of VEFG-A and its isoforms.

20. The hetero-dimeric modified ubiquitin protein according to claim 1, wherein said modified ubiquitin monomers have an amino acid identity to SEQ ID NO: 1 of at least 85%.

21. The hetero-dimeric modified ubiquitin protein according to claim 6, wherein said modified ubiquitin monomers have an amino acid identity to SEQ ID NO: 1 of at least 85%.

* * * * *